(12) United States Patent
Mansi et al.

(10) Patent No.: US 11,488,299 B2
(45) Date of Patent: Nov. 1, 2022

(54) METHOD AND SYSTEM FOR COMPUTER-AIDED TRIAGE

(71) Applicant: Viz.ai Inc., San Francisco, CA (US)

(72) Inventors: Christopher Mansi, San Francisco, CA (US); David Golan, San Francisco, CA (US)

(73) Assignee: Viz.ai Inc., San Francisco, CA (US)

( * ) Notice: Subject to any disclaimer, the term of this patent is extended or adjusted under 35 U.S.C. 154(b) by 103 days.

(21) Appl. No.: 16/917,415

(22) Filed: Jun. 30, 2020

(65) Prior Publication Data

US 2020/0334811 A1 Oct. 22, 2020

Related U.S. Application Data

(63) Continuation of application No. 16/688,721, filed on Nov. 19, 2019, now Pat. No. 10,733,730, which is a
(Continued)

(51) Int. Cl.
*G06K 9/00* (2022.01)
*G06T 7/00* (2017.01)
(Continued)

(52) U.S. Cl.
CPC .......... *G06T 7/0012* (2013.01); *A61B 5/4064* (2013.01); *G06T 7/11* (2017.01); *G16H 30/20* (2018.01); *G16H 30/40* (2018.01); *G16H 40/20* (2018.01); *G16H 50/20* (2018.01); *G16H 80/00* (2018.01); *H04L 67/12* (2013.01); *A61B 5/002* (2013.01); *A61B 5/02007* (2013.01); *A61B 5/7264* (2013.01);

*G06T 2207/10016* (2013.01); *G06T 2207/10081* (2013.01); *G06T 2207/10088* (2013.01); *G06T 2207/20072* (2013.01);
(Continued)

(58) Field of Classification Search
None
See application file for complete search history.

(56) References Cited

U.S. PATENT DOCUMENTS

| 6,349,330 B1 | 2/2002 | Bernadett et al. |
| 8,374,414 B2 | 2/2013 | Tang et al. |

(Continued)

FOREIGN PATENT DOCUMENTS

| JP | 2004243117 A | 9/2004 |
| JP | 4854717 B2 | 11/2011 |

(Continued)

OTHER PUBLICATIONS

Yu Y. et al., "Use of Deep Learning to Predict Final Ischemic Stroke Lesions From Initial Magnetic Resonance Imaging", Mar. 1, 2020, https://europepmc.org/article/med/32163165.
(Continued)

*Primary Examiner* — Wei Wen Yang
(74) *Attorney, Agent, or Firm* — Jeffrey Schox; Caitlin Ploch

(57) ABSTRACT

A system for computer-aided triage can include a router, a remote computing system, and a client application. A method for computer-aided triage can include determining a parameter associated with a data packet, determining a treatment option based on the parameter, and transmitting information to a device associated with a second point of care.

20 Claims, 11 Drawing Sheets

Related U.S. Application Data continuation-in-part of application No. 16/418,908, filed on May 21, 2019, now Pat. No. 10,614,572, which is a continuation of application No. 16/012,495, filed on Jun. 19, 2018, now Pat. No. 10,346,979, said application No. 16/418,908 is a continuation of application No. 16/012,458, filed on Jun. 19, 2018, now Pat. No. 10,373,315.

(60) Provisional application No. 62/535,970, filed on Jul. 24, 2017, provisional application No. 62/535,973, filed on Jul. 24, 2017, provisional application No. 62/521,968, filed on Jun. 19, 2017.

(51) Int. Cl.

| | | |
|---|---|---|
| *G16H 80/00* | (2018.01) | |
| *G16H 30/40* | (2018.01) | |
| *G16H 50/20* | (2018.01) | |
| *G16H 30/20* | (2018.01) | |
| *G16H 40/20* | (2018.01) | |
| *H04L 67/12* | (2022.01) | |
| *G06T 7/11* | (2017.01) | |
| *A61B 5/00* | (2006.01) | |
| *A61B 5/02* | (2006.01) | |

(52) U.S. Cl.
CPC ............... *G06T 2207/20076* (2013.01); *G06T 2207/20081* (2013.01); *G06T 2207/30016* (2013.01); *G06T 2207/30101* (2013.01); *G06T 2207/30172* (2013.01)

(56) References Cited

U.S. PATENT DOCUMENTS

| | | | |
|---|---|---|---|
| 9,307,918 | B2 | 4/2016 | Kinrot et al. |
| 9,439,622 | B2 | 9/2016 | Case et al. |
| 10,346,979 | B2 | 7/2019 | Mansi et al. |
| 10,373,315 | B2 | 8/2019 | Mansi et al. |
| 10,835,257 | B2 | 11/2020 | Ferrera et al. |
| 2004/0161137 | A1 | 8/2004 | Aben et al. |
| 2006/0140473 | A1 | 6/2006 | Brooksby et al. |
| 2008/0021502 | A1 | 1/2008 | Imielinska et al. |
| 2009/0279752 | A1 | 11/2009 | Sirohey et al. |
| 2010/0106002 | A1 | 4/2010 | Sugiyama et al. |
| 2011/0028825 | A1 | 2/2011 | Douglas et al. |
| 2011/0172550 | A1 | 7/2011 | Martin et al. |
| 2012/0065987 | A1 | 3/2012 | Farooq et al. |
| 2013/0208955 | A1* | 8/2013 | Zhao .................... G06T 7/0012 382/128 |
| 2013/0208966 | A1 | 8/2013 | Zhao et al. |
| 2014/0142982 | A1 | 5/2014 | Janssens |
| 2014/0142983 | A1 | 5/2014 | Backhaus et al. |
| 2014/0222444 | A1 | 8/2014 | Cerello et al. |
| 2015/0104102 | A1 | 4/2015 | Carreira et al. |
| 2015/0320365 | A1 | 11/2015 | Schulze et al. |
| 2016/0037057 | A1 | 2/2016 | Westin et al. |
| 2016/0063191 | A1 | 3/2016 | Vesto et al. |
| 2016/0100302 | A1 | 4/2016 | Barash et al. |
| 2016/0135706 | A1 | 5/2016 | Sullivan et al. |
| 2016/0180042 | A1 | 6/2016 | Menon et al. |
| 2016/0188829 | A1 | 6/2016 | Southerland et al. |
| 2017/0007167 | A1 | 1/2017 | Kostic et al. |
| 2017/0143428 | A1 | 5/2017 | Raffy et al. |
| 2017/0147765 | A1 | 5/2017 | Mehta |
| 2017/0181657 | A1 | 6/2017 | Jin et al. |
| 2017/0228516 | A1 | 8/2017 | Sampath et al. |
| 2017/0258433 | A1 | 9/2017 | Gulsun et al. |
| 2017/0300654 | A1 | 10/2017 | Stein et al. |
| 2017/0340260 | A1 | 11/2017 | Chowdhury et al. |
| 2018/0025255 | A1 | 1/2018 | Poole et al. |
| 2018/0046759 | A1 | 2/2018 | Barral |
| 2018/0085001 | A1 | 3/2018 | Berger et al. |
| 2018/0110475 | A1 | 4/2018 | Shaya |
| 2018/0116620 | A1 | 5/2018 | Chen et al. |
| 2018/0253530 | A1 | 9/2018 | Goldberg et al. |
| 2018/0365824 | A1 | 12/2018 | Yuh et al. |
| 2019/0198160 | A1 | 6/2019 | Barral |
| 2019/0380643 | A1 | 12/2019 | Kochura et al. |
| 2020/0058410 | A1 | 2/2020 | Khouri et al. |
| 2020/0294241 | A1 | 9/2020 | Wu et al. |
| 2020/0364587 | A1 | 11/2020 | Kapur et al. |
| 2022/0087631 | A1 | 3/2022 | D'Esterre et al. |
| 2022/0130547 | A1 | 4/2022 | Grady et al. |
| 2022/0180518 | A1 | 6/2022 | Agus et al. |

FOREIGN PATENT DOCUMENTS

| | | |
|---|---|---|
| JP | 2012027565 A | 2/2012 |
| WO | 2016134125 A1 | 8/2016 |

OTHER PUBLICATIONS

Lewis et al., "Ambulance smartphone tool—accuracy" BMJ, 2016, pp. 1-5 (Year: 2016).

Kirisil, H.A., et al., "Standardized evaluation framework for evaluating coronary artery stenosis detection, stenosis quantification and lumen segmentation algorithms in computed tomography angiography", Elsevier, 2013, pp. 859-876.

Smith, Wade S., et al., "Prognostic Significance of Angiographically Confirmed Large Vessel Intracranial Occlusion in Patients Presenting With Acute Brain Ischemia", Neurocritical Care, vol. 4, 2006.

Kristina Lidayova et al. "Skeleton-based 1-3,6-15 fast, fully automated generation of vessel tree structure for clinical evaluation of blood vessel systems" In: "Skeletonization : theory, methods and applications", Jun. 1, 2017 (Jun. 1, 2017).

Madhuripnaiknh Ile T al: "Computed Tomography Angiography in Head and Neck Emergencies", Seminar in Ultrasound, US, vol. 38, No. 4, Feb. 20, 2017 (Feb. 20, 2017), pp. 345-356.

Gupta, Akshat, et al., "Delineation of Ischemic Core and Penumbra Volumes from MRI using MSNet Architecture", Annu Int Conf IEEE Eng Med Biol Soc. Jul. 2019;2019:6730-6733.

Kuang, Hulin, et al., "Segmenting Hemorrhagic and Ischemic Infarct Simultaneously From Follow-Up Non-Contrast CT Images in Patients With Acute Ischemic Stroke", IEEE Access, vol. 7, 22, May 2019.

Mittal, Sushil, et al., "Fast Automatic Detection of Calcified Coronary Lesions in 3D Cardiac CT Images", MLMI 2010, pp. 1-9.

Zerna, C., et al., "Imaging, Intervention, and Workflow in Acute Ischemic Strike: The Calgary Approach", AJNR M J Neuroradiol 37.978-84, Jun. 2016, pp. 978-984.

\* cited by examiner

METHOD AND SYSTEM FOR COMPUTER-AIDED TRIAGE

CROSS-REFERENCE TO RELATED APPLICATIONS

This application is a continuation of U.S. application Ser. No. 16/688,721, filed 19 Nov. 2019, which is a continuation-in-part of U.S. application Ser. No. 16/418,908, filed 21 May 2019, which is a continuation of U.S. application Ser. No. 16/012,495, filed 19 Jun. 2018, which claims the benefit of U.S. Provisional Application No. 62/535,973, filed 24 Jul. 2017, U.S. Provisional Application No. 62/535,970, filed 24 Jul. 2017, and U.S. Provisional Application No. 62/521,968, filed 19 Jun. 2017, each of which is incorporated in its entirety by this reference. U.S. application Ser. No. 16/418,908, filed 21 May 2019, is also a continuation of U.S. application Ser. No. 16/012,458, filed 19 Jun. 2018, which claims the benefit of U.S. Provisional Application No. 62/535,973, filed 24 Jul. 2017, U.S. Provisional Application No. 62/535,970, filed 24 Jul. 2017, and U.S. Provisional Application No. 62/521,968, filed 19 Jun. 2017, each of which is incorporated in its entirety by this reference.

TECHNICAL FIELD

This invention relates generally to the medical diagnostic field, and more specifically to a new and useful system and method for computer-aided triage in the medical diagnostic field.

BACKGROUND

In current triaging workflows, especially those in an emergency setting, a patient presents at a first point of care, where an assessment, such as imaging, is performed. The image data is then sent to a standard radiology workflow, which typically involves: images being uploaded to a radiologist's queue, the radiologist reviewing the images at a workstation, the radiologist generating a report, an emergency department doctor reviewing the radiologist's report, the emergency department doctor determining and contact a specialist, and making a decision of how to treat and/or transfer the patient to a $2^{nd}$ point of care. This workflow is typically very time-consuming, which increases the time it takes to treat and/or transfer a patient to a specialist. In many conditions, especially those involving stroke, time is extremely sensitive, as it is estimated that in the case of stroke, a patient loses about 1.9 million neurons per minute that the stroke is left untreated (Saver et al.). Further, as time passes, the amount and types of treatment options, such as a mechanical thrombectomy, decrease.

Thus, there is a need in the triaging field to create an improved and useful system and method for decreasing the time it takes to determine and initiate treatment for a patient presenting with a critical condition.

DESCRIPTION OF THE PREFERRED EMBODIMENTS

The following description of the preferred embodiments of the invention is not intended to limit the invention to these preferred embodiments, but rather to enable any person skilled in the art to make and use this invention.

1. Overview

Figure 1:
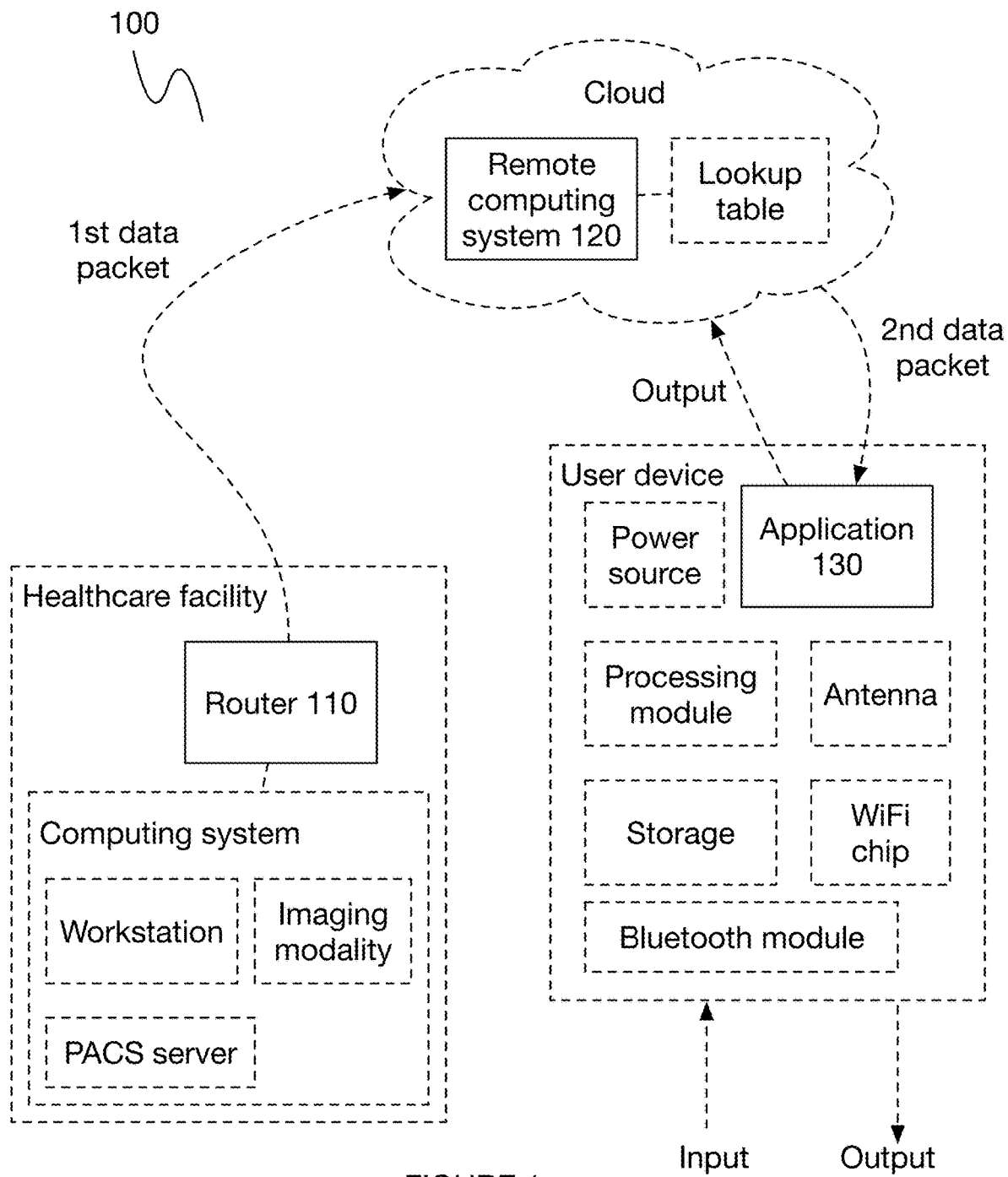
FIG. 1 is a schematic of a system for computer-aided triage.

As shown in FIG. 1, a system 100 for computer-aided triage includes a router 110, a remote computing system 120, and a client application 130. Additionally or alternatively, the system 100 can include any number of computing systems (e.g., local, remote), servers (e.g., PACS server), storage, lookup table, memory, or any other suitable components.

Figure 2:
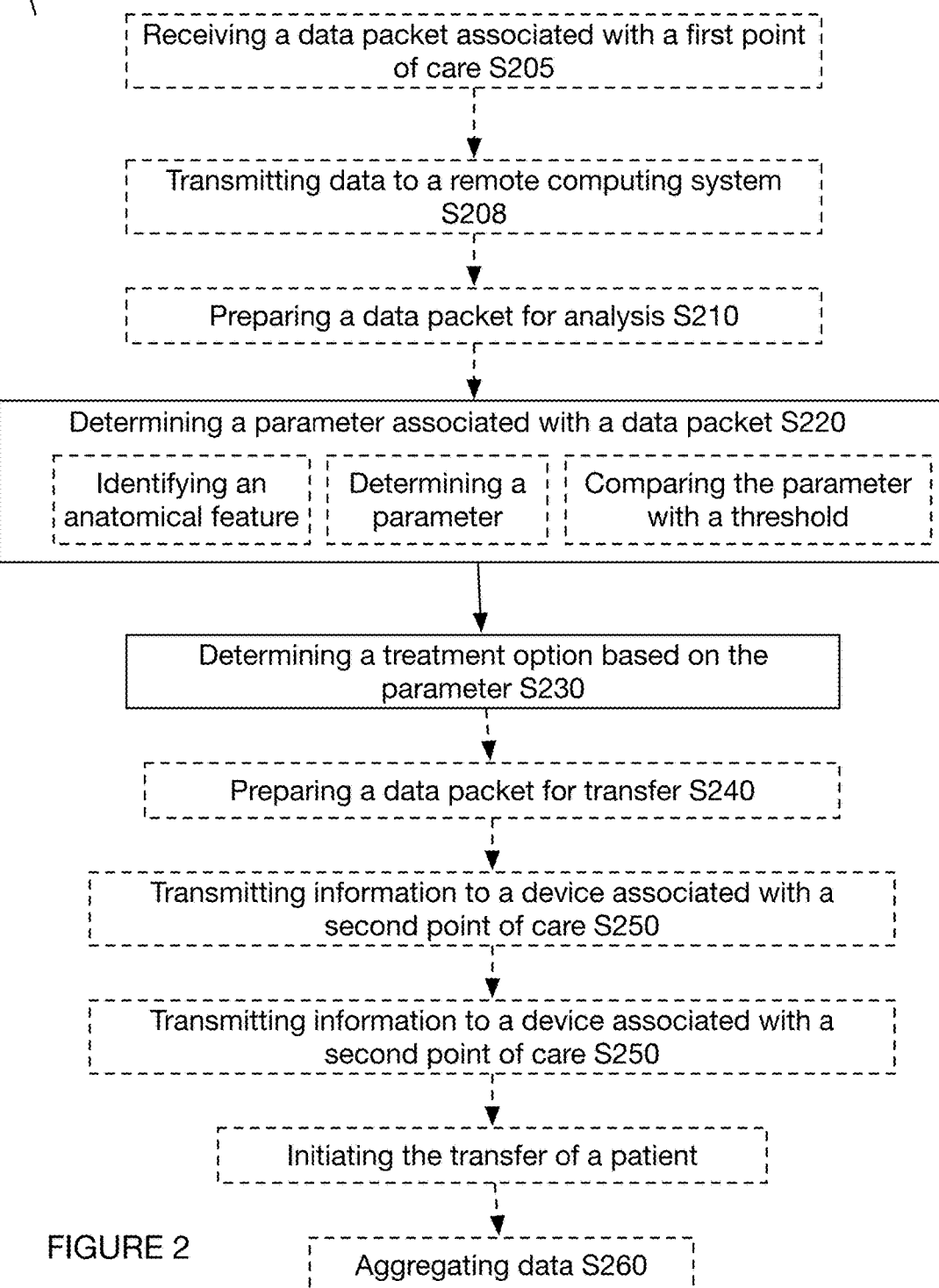
FIG. 2 is a schematic of a method for computer-aided triage.

As shown in FIG. 2, method 200 for computer-aided triage includes determining a parameter associated with a data packet S220, determining a treatment option based on the parameter S230, and transmitting information to a device associated with a second point of care S250. Additionally or alternatively, the method 200 can include any or all of: receiving a data set at a first point of care S205, transmitting data to a remote computing system S208, preparing a data packet for analysis S210, preparing a data packet for transfer S240, aggregating data S260, or any other suitable steps performed in any suitable order.

2. Benefits

The system and method for computer-aided triage can confer several benefits over current systems and methods.

In some variations, the system and/or method confer the benefit of reducing the time to match and/or transfer a patient presenting with a condition (e.g., stroke, LVO) to a specialist. In some examples, for instance, the average time between generating a computed tomography angiography (CTA) dataset and notifying a specialist is reduced (e.g., from over 50 minutes to less than 8 minutes).

In some variations, the method provides a parallel process to a traditional workflow (e.g., standard radiology workflow), which can confer the benefit of reducing the time to determine a treatment option while having the outcome of the traditional workflow as a backup in the case that an inconclusive or inaccurate determination (e.g., false negative, false positive, etc.) results from the method.

In some variations, the method is configured to have a high sensitivity (e.g., 87.8%, approximately 88%, between 81% and 93%, greater than 87%, etc.), which functions to detect a high number of true positive cases and help these patients reach treatment faster. In the event that this results in a false positive, only a minor disturbance—if any—is caused to a specialist, which affects the specialist's workflow negligibly (e.g., less than 5 minutes), if at all. Additionally or alternatively, the method can be configured to have a high specificity (e.g., 89.6%, approximately 90%, between 83% and 94%, greater than 89%, etc.), which can reduce a probability of determining a false negative.

In some variations, the method confers the benefit of reorganizing a queue of patients, wherein patients having a certain condition are detected early and prioritized (e.g., moved to the front of the queue).

In some variations, the method confers the benefit of determining actionable analytics to optimize a workflow, such as an emergency room triage workflow.

In some variations, the method and/or system confers the benefit of identifying a patient suited for a particular clinical trial. In specific examples, an assessment of the patient can be used to check for the patient's eligibility for a clinical trial, and can optionally initiate any suitable triggers (e.g., notifying the patient, sending the patient information regarding the clinical trial, notifying a principal investigator [PI] for the clinical trial, etc.). This can, in turn, enable any or all of: an increase in the number of individuals recommended for a clinical trial, a better match between the individuals recommended for a clinical trial and the objectives of the clinical trial, a reduction in the number of individuals who are recommended for a clinical trial but do not qualify, and/or any other suitable outcome(s).

Additionally or alternatively, the system and method can confer any other benefit.

3. System

The system 100 for computer-aided triage, as shown in FIG. 1, includes a router 110, remote computing system 120, and a client application 130. Additionally or alternatively, the system 100 can include any number of computing systems (e.g., local, remote), servers (e.g., PACS server), storage, lookup table, memory, or any other suitable components.

The system 100 can implement any or all of the method 200 or any other suitable method.

The system 100 preferably interfaces with one or more points of care (e.g., $1^{st}$ point of care, $2^{nd}$ point of care, $3^{rd}$ point of care, etc.), which are each typically a healthcare facility. A $1^{st}$ point of care herein refers to the healthcare facility to which a patient presents, typically where the patient first presents (e.g., in an emergency setting). Conventionally, healthcare facilities include spoke facilities, which are often general (e.g., non-specialist, emergency, etc.) facilities, and hub (e.g., specialist) facilities, which can be equipped or better equipped (e.g., in comparison to spoke facilities) for certain procedures (e.g., mechanical thrombectomy), conditions, or patients. Patients typically present to a spoke facility at a $1^{st}$ point of care, but can alternatively present to a hub facility, such as when it is evident what condition their symptoms reflect, when they have a prior history of a serious condition, when the condition has progressed to a high severity, when a hub facility is closest, randomly, or for any other reason. A healthcare facility can include any or all of: a hospital, clinic, ambulances, doctor's office, imaging center, laboratory, primary stroke center (PSC), comprehensive stroke center (CSC), stroke ready center, interventional ready center, or any other suitable facility involved in patient care and/or diagnostic testing.

A patient can be presenting with symptoms of a condition, no symptoms (e.g., presenting for routine testing), or for any other suitable system. In some variations, the patient is presenting with one or more stroke symptoms (e.g., ischemic stroke symptoms), such as, but not limited to, weakness, numbness, speech abnormalities, and facial drooping. Typically, these patients are then treated in accordance with a stroke protocol, which typically involves an imaging protocol at an imaging modality, such as, but not limited to, a non-contrast CT (NCCT) scan of the head, CTA of the head and neck, CT perfusion (CTP) of the head.

A healthcare worker herein refers to any individual or entity associated with a healthcare facility, such as, but not limited to: a physician, emergency room physician (e.g., orders appropriate lab and imaging tests in accordance with a stroke protocol), radiologist (e.g., on-duty radiologist, healthcare worker reviewing a completed imaging study, healthcare working authoring a final report, etc.), neuroradiologist, specialist (e.g., neurovascular specialist, vascular neurologist, neuro-interventional specialist, neuro-endovascular specialist, expert/specialist in a procedure such as mechanical thrombectomy, cardiac specialist, etc.), administrative assistant, healthcare facility employee (e.g., staff employee), emergency responder (e.g., emergency medical technician), or any other suitable individual.

The image data can include computed tomography (CT) data (e.g., radiographic CT, non-contrast CT, CT perfusion, etc.), preferably CT angiography (CTA) data (e.g., axial data, axial series, etc.) but can additionally or alternatively any other suitable image data. The image data is preferably generated at an imaging modality (e.g., scanner at the $1^{st}$ point of care), such as a CT scanner, magnetic resonance imaging (MRI) scanner, ultrasound system, or any other scanner. Additionally or alternatively, image data can be generated from a camera, user device, accessed from a database or web-based platform, drawn, sketched, or otherwise obtained.

3.1 System—Router 110

The system 100 can include a router 110 (e.g., medical routing system), which functions to receive a data packet (e.g., dataset) including instances (e.g., images, scans, etc.) taken at an imaging modality (e.g., scanner) via a computing system (e.g., scanner, workstation, PACS server) associated with a $1^{st}$ point of care. The instances are preferably in the Digital Imaging and Communications in Medicine (DICOM) file format, as well as generated and transferred between computing system in accordance with a DICOM protocol, but can additionally or alternatively be in any suitable format. Additionally or alternatively, the instances can include any suitable medical data (e.g., diagnostic data, patient data, patient history, patient demographic information, etc.), such as, but not limited to, PACS data, Health-Level 7 (HL7) data, electronic health record (EHR) data, or any other suitable data, and to forward the data to a remote computing system.

The instances preferably include (e.g., are tagged with) and/or associated with a set of metadata, but can additionally or alternatively include multiple sets of metadata, no metadata, extracted (e.g., removed) metadata (e.g., for regulatory purposes, HIPAA compliance, etc.), altered (e.g., encrypted, decrypted, etc.) metadata, or any other suitable metadata, tags, identifiers, or other suitable information.

The router 110 can refer to or include a virtual entity (e.g., virtual machine, virtual server, etc.) and/or a physical entity (e.g., local server). The router can be local (e.g., at a $1^{st}$ healthcare facility, $2^{nd}$ healthcare facility, etc.) and associated with (e.g., connected to) any or all of: on-site server associated with any or all of the imaging modality, the healthcare facility's PACS architecture (e.g., server associated with physician workstations), or any other suitable local server or DICOM compatible device(s). Additionally or alternatively, the router can be remote (e.g., locate at a remote facility, remote server, cloud computing system, etc.), and associated with any or all of: a remote server associated with the PACS system, a modality, or another DICOM compatible device such as a DICOM router.

The router 110 preferably operates on (e.g., is integrated into) a system (e.g., computing system, workstation, server, PACS server, imaging modality, scanner, etc.) at a $1^{st}$ point of care but additionally or alternatively, at a $2^{nd}$ point of care, remote server (e.g., physical, virtual, etc.) associated with one or both of the $1^{st}$ point of care and the $2^{nd}$ point of care (e.g., PACS server, EHR server, HL7 server), a data storage system (e.g., patient records), or any other suitable system. In some variations, the system that the router operates on is physical (e.g., physical workstation, imaging modality, scanner, etc.) but can additionally or alternatively include virtual components (e.g., virtual server, virtual database, cloud computing system, etc.).

The router no is preferably configured to receive data (e.g., instances, images, study, series, etc.) from an imaging modality, preferably an imaging modality (e.g., CT scanner, MRI scanner, ultrasound machine, etc.) at a first point of care (e.g., spoke, hub, etc.) but can additionally or alternatively be at a second point of care (e.g., hub, spoke, etc.), multiple points of care, or any other healthcare facility. The router can be coupled in any suitable way (e.g., wired connection, wireless connection, etc.) to the imaging modality (e.g., directly connected, indirectly connected via a PACS server, etc.). Additionally or alternatively, the router 100 can be connected to the healthcare facility's PACS architecture, or other server or DICOM-compatible device of any point of care or healthcare facility.

In some variations, the router includes a virtual machine operating on a computing system (e.g., computer, workstation, user device, etc.), imaging modality (e.g., scanner), server (e.g., PACS server, server at $1^{st}$ healthcare facility, server at $2^{nd}$ healthcare facility, etc.), or other system. In a specific example, the router is part of a virtual machine server. In another specific example, the router is part of a local server.

3.2 System—Remote Computing System 120

The system 100 can include a remote computing system 120, which can function to receive and process data packets (e.g., dataset from router), determine a treatment option (e.g., select a $2^{nd}$ point of care, select a specialist, etc.), interface with a user device (e.g., mobile device), compress a data packet, extract and/or remove metadata from a data packet (e.g., to comply with a regulatory agency), or perform any other suitable function.

Preferably, part of the method 200 is performed at the remote computing system (e.g., cloud-based), but additionally or alternatively all of the method 200 can be performed at the remote computing system, the method 200 can be performed at any other suitable computing system(s). In some variations, the remote computing system 120 provides an interface for technical support (e.g., for a client application) and/or analytics. In some variations, the remote computing system includes storage and is configured to store and/or access a lookup table, wherein the lookup table functions to determine a treatment option (e.g., $2^{nd}$ point of care), a contact associated with the $2^{nd}$ point of care, and/or any other suitable information.

In some variations, the remote computing system 120 connects multiple healthcare facilities (e.g., through a client application, through a messaging platform, etc.).

In some variations, the remote computing system 120 functions to receive one or more inputs and/or to monitor a set of client applications (e.g., executing on user devices, executing on workstations, etc.).

3.3 System—Application 130

Figure 5A:
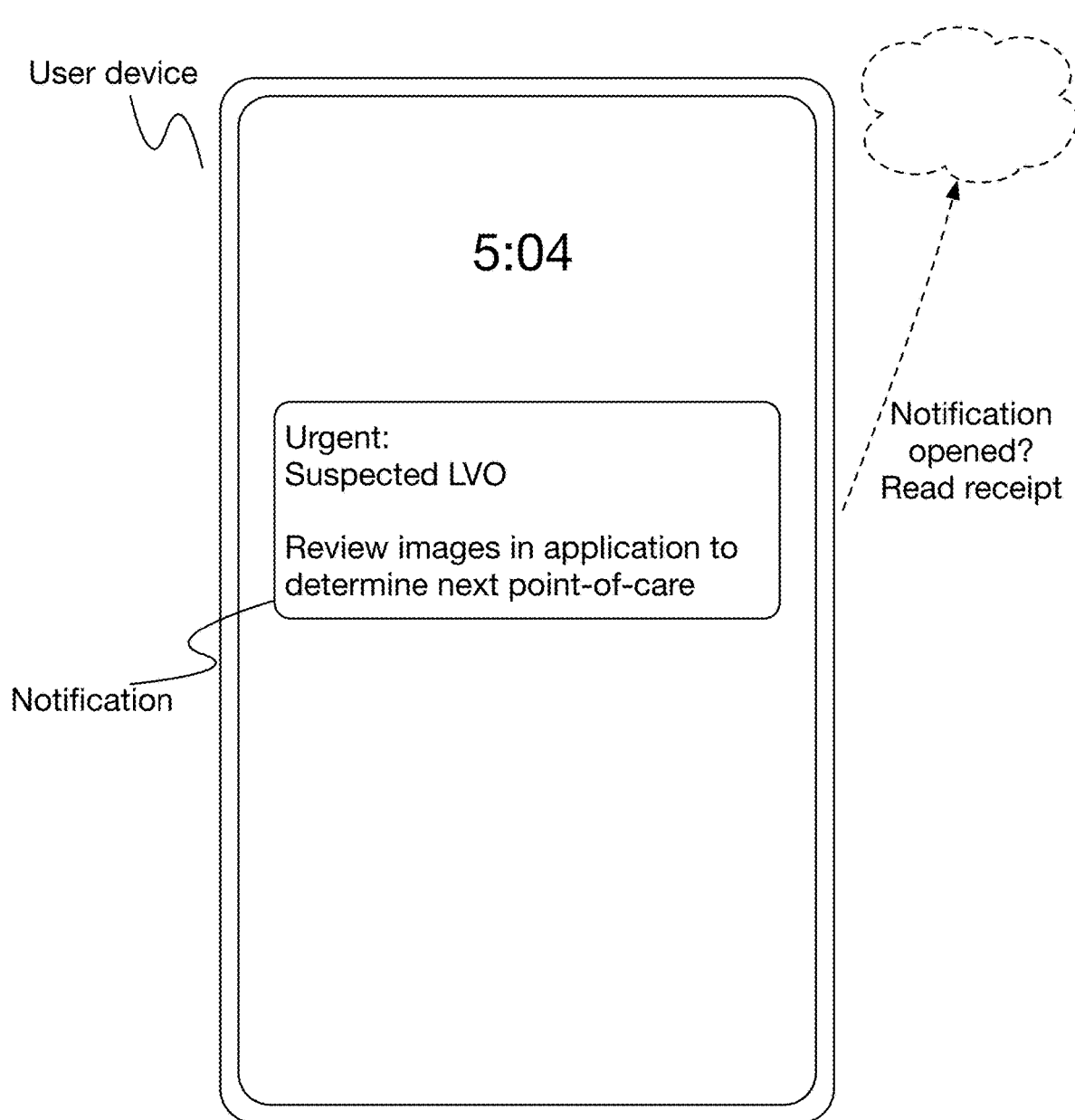
FIGS. 5A and 5B depict a variation of an application on a user device.
Figure 5B:
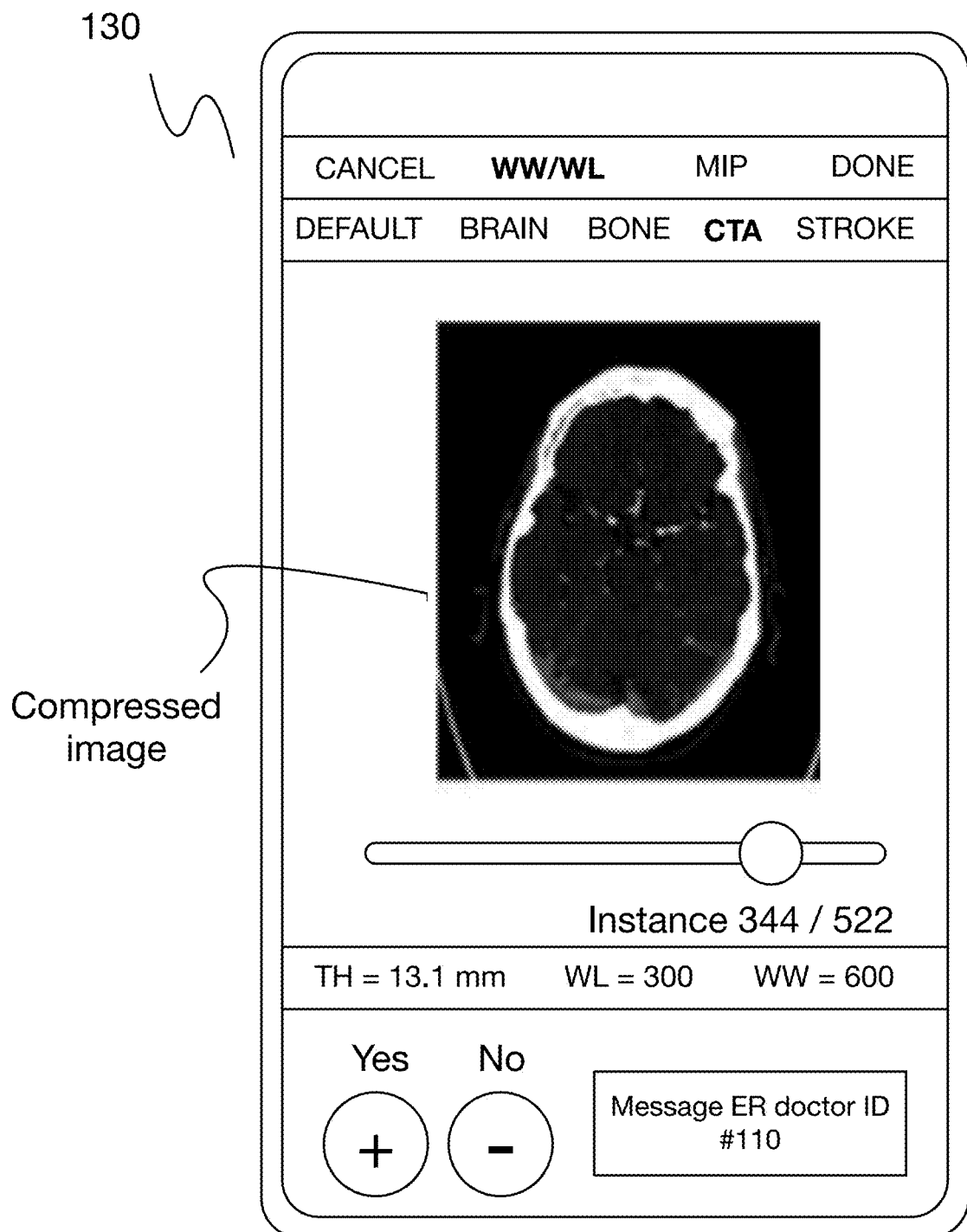

The system 100 can include one or more applications 130 (e.g., clients, client applications, client application executing on a device, etc.), such as the application shown in FIGS. 5A and 5B, which individually or collectively function to provide one or more outputs (e.g., from the remote computing system) to a contact. Additionally or alternatively, they can individually or collectively function to receive one or more inputs from a contact, provide one or more outputs to a healthcare facility (e.g., first point of care, second point of care, etc.), establish communication between healthcare facilities, or perform any other suitable function.

In some variations, one or more features of the application (e.g., appearance, information content, information displayed, user interface, graphical user interface, etc.) are determined based on any or all of: what kind of device the application is operating on (e.g., user device vs. healthcare facility device, mobile device vs. stationary device), where the device is located (e.g., $1^{st}$ point of care, $2^{nd}$ point of care, etc.), who is interacting with the application (e.g., user identifier, user security clearance, user permission, etc.), whether the device is associated with an individual involved in the treatment of the individual versus an individual involved in a clinical trial, or any other characteristic. In some variations, for instance, an application executing on a healthcare facility will display a $1^{st}$ set of information (e.g., uncompressed images, metadata, etc.) while an application executing on a user device will display a $2^{nd}$ set of information (e.g., compressed images, no metadata, etc.). In some variations, the type of data to display is determined based on any or all of: an application identifier, mobile device identifier, workstation identifier, or any other suitable identifier.

The outputs of the application can include any or all of: an alert or notification (e.g., push notification, text message, call, email, etc.), an image set, a set of tools for interacting with the image set (e.g., panning, zooming, rotating, window leveling, scrolling, maximum intensity projection, changing orientation of 3D scan, etc.), a messaging platform (e.g., text, video, etc.), a telecommunication platform, directory of contact information (e.g., $1^{st}$ point of care contact info, $2^{nd}$ point of care contact info, etc.), tracking of a workflow or activity (e.g., real-time or near real-time updates of patient status/workflow/etc.), analytics based on or related to the tracking (e.g., predictive analytics such as predicted time remaining in radiology workflow or predicted time until stroke reaches a certain severity, average time in a workflow, average time to transition to a second point of care, etc.), a recommendation for the recipient to further investigate the patient as a candidate for clinical trial, information associated with the patient's eligibility and/or willingness to participate in a clinical trial (e.g., patient demographic information, patient consent for a clinical trial, contact information of the patient, etc.), a patient's and/or a physician's consent for a clinical trial, or any other suitable output.

The inputs can include any or all of the outputs described previously, touch inputs (e.g., received at a touch-sensitive surface), audio inputs, optical inputs, or any other suitable input. The set of inputs preferably includes an input indicating receipt of an output by a contact. This can include an active input from the contact (e.g., contact makes selection at application), a passive input (e.g., read receipt), or any other input. One or more inputs can optionally trigger an action, such as the transmission of a consent form to the patient and/or to any other suitable user (e.g., specialist associated with the patient, healthcare worker or administrator at a first point of care, healthcare worker or administrator at a second point of care, etc.). In variations involving the recommendation of a patient for a clinical trial, for instance, upon reviewing an output, an individual associated with a clinical trial can indicate (e.g., by selecting "interested," by swiping, etc.) that he or she is interested in recruiting the patient, which can trigger the transmission of a consent form for the patient to participate in the clinical trial. Receiving a signed or otherwise accepted consent form (e.g., at a user device of a research coordinator, at a user device of a healthcare worker associated with the patient, at a remote server, at a local server, etc.) can optionally trigger one or more outputs, such as any or all of: the transmission of additional information (e.g., images, patient information, private information, etc.) to the research coordinator (e.g., to a mobile user device, to a stationary user device, etc.); accessibility of additional information to the research coordinator (e.g., at the client application, at a remote server, etc.); communication with a healthcare worker (e.g., specialist, administrator, etc.) associated with the patient (e.g., to update the research coordinator on the status of the patient, to provide an estimated time and place of arrival of the patient at a second point of care, to answer questions asked by the research coordinator, to answer questions asked by the healthcare worker, etc.); and/or any other suitable outputs.

A research coordinator preferably refers to an individual or group of individuals involved in any or all of: organization, recruitment, and/or communication in research studies or clinical trials. The research coordinator can be any or all of: a researcher, administrator, clinician (e.g., clinical specialist, clinician involved in decision-making and/or treatment of the patient, clinician not involved in decision-making and/or treatment of the patient, etc.), and/or any other individual. Additionally or alternatively, the research coordinator can work with any or all of the above individuals (e.g., a researcher or administrator collaborating with a clinical specialist on the clinical trial). Further additionally or alternatively, the research coordinator can be any other individual described above or below, and/or any other suitable individual(s).

In one variation, the system 100 includes a mobile device application 130 and a workstation application 130—both connected to the remote computing system—wherein a shared user identifier (e.g., specialist account, user account, etc.) can be used to connect the applications (e.g., retrieve a case, image set, etc.) and determine the information to be displayed at each application (e.g., variations of image datasets). In one example, the information to be displayed (e.g., compressed images, high-resolution images, etc.) can be determined based on: the system type (e.g., mobile device, workstation), the application type (e.g., mobile device application, workstation application,), the user account (e.g., permissions, etc.), any other suitable information, or otherwise determined.

The application can include any suitable algorithms or processes for analysis, and part or all of the method 200 can be performed by a processor associated with the application.

The application preferably includes both front-end (e.g., application executing on a user device, application executing on a workstation, etc.) and back-end components (e.g., software, processing at a remote computing system, etc.), but can additionally or alternatively include just front-end or back-end components, or any number of components implemented at any suitable system(s).

3.4 System—Additional Components

The system 100 and/or or any component of the system 100 can optionally include or be coupled to any suitable component for operation, such as, but not limited to: a processing module (e.g., processor, microprocessor, etc.), control module (e.g., controller, microcontroller), power module (e.g., power source, battery, rechargeable battery, mains power, inductive charger, etc.), sensor system (e.g., optical sensor, camera, microphone, motion sensor, location sensor, etc.), or any other suitable component.

3.5 System—Variations

In one variation, the system includes a router 110, which operates at a computing system at a $1^{st}$ point of care and receives image data from an imaging modality. The router transmits the image data to a remote computing system, wherein a series of algorithms (e.g., machine learning algorithms) are performed at the remote computing system, which determines a hypothesis for whether or not a suspected condition is present based on the image data and/or any associated metadata. Based on the determination, a contact is determined from a lookup table (e.g., in storage at the remote computing system), wherein the contact is notified at a user device (e.g., personal device) and sent image data through a client application executing on the user device. One or more inputs from the contact at the application can be received at the remote computing system, which can be used to determine a next point of care for the patient.

4. Method

As shown in FIG. 2, the method 200 includes determining a parameter associated with a data packet S220, determining a treatment option based on the parameter S230, and transmitting information to a device associated with a second point of care S250. Additionally or alternatively, the method 200 can include any or all of: receiving a data set at a first point of care S205, transmitting data to a remote computing system S208, preparing a data packet for analysis S210, preparing a data packet for transfer S240, aggregating data S260, or any other suitable steps performed in any suitable order.

Figure 3:
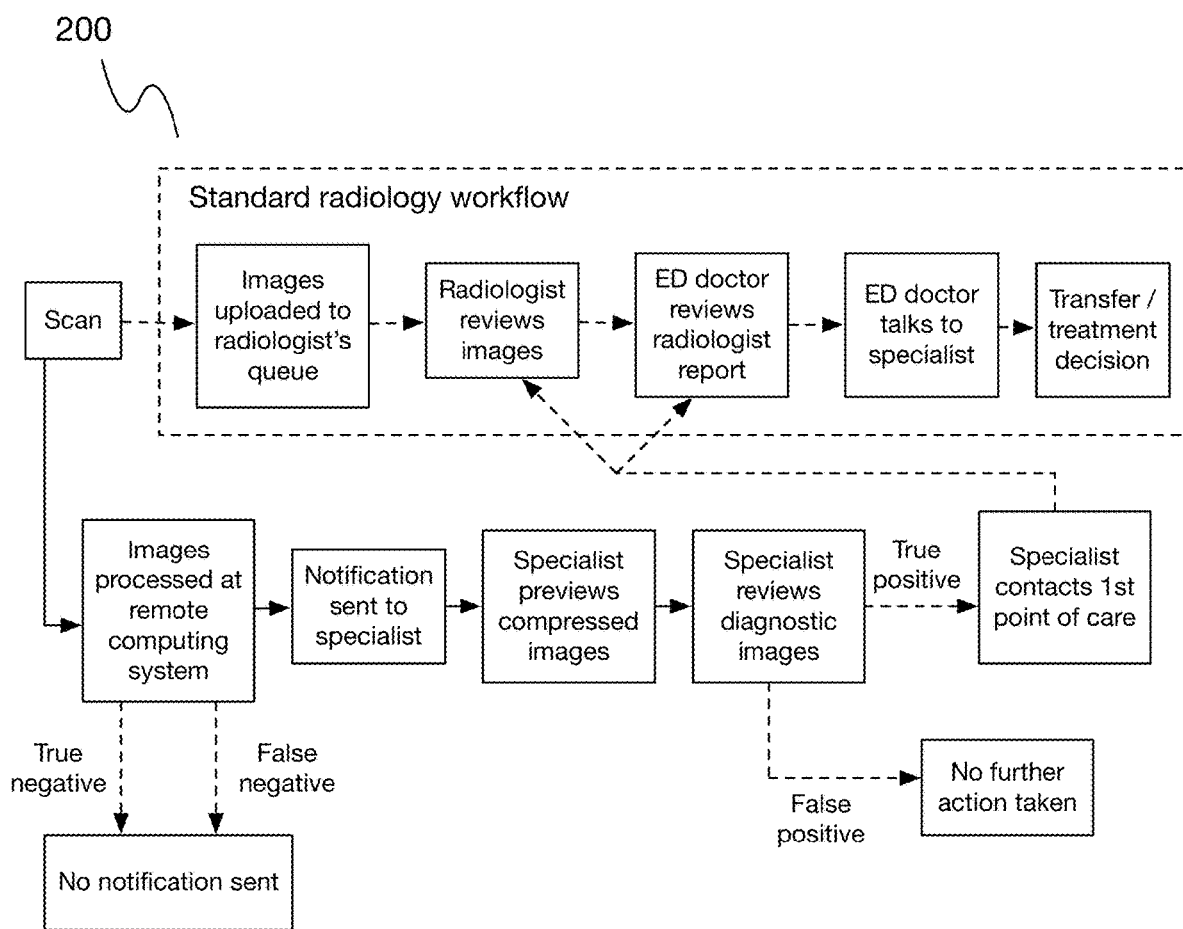
FIG. 3 depicts a variation of a method for computer-aided triage.

The method 200 is preferably performed separate from but in parallel with (e.g., contemporaneously with, concurrently with, etc.) a standard radiology workflow (e.g., as shown in FIG. 3), but can additionally or alternatively be implemented within a standard workflow, be performed at a separate time with respect to a standard workflow, or be performed at any suitable time.

The method 200 can be partially or fully implemented with the system 100 or with any other suitable system.

The method 200 functions to improve communication across healthcare facility networks (e.g., stroke networks, spokes and hubs, etc.) and decrease the time required to transfer a patient having a suspected time-sensitive condition (e.g., brain condition, stroke, ischemic stroke, large vessel occlusion (LVO), cardiac event, trauma, etc.) from a first point of care (e.g., spoke, non-specialist facility, stroke center, ambulance, etc.) to a second point of care (e.g., hub, specialist facility, comprehensive stroke center, etc.), wherein the second point of care refers to a healthcare facility equipped to treat the patient. In some variations, the second point of care is the first point of care, wherein the patient is treated at the healthcare facility to which he or she initially presents. Additionally or alternatively, the method 200 can function to recruit patients (e.g., well-suited, fulfilling a set of criteria, etc.) for a clinical trial.

The method 200 preferably functions as a parallel workflow tool, wherein the parallel workflow is performed contemporaneously with (e.g., concurrently, during, partially during) a standard radiology workflow (e.g., radiologist queue), but can additionally or alternatively be implemented within a standard workflow (e.g., to automate part of a standard workflow process, decrease the time required to perform a standard workflow process, etc.), be performed during a workflow other than a radiology workflow (e.g., during a routine examination workflow), or at any other suitable time.

In variations involving the recommendation of a patient for a clinical trial, the method 200 can be performed at any or all of: in parallel (e.g., in parallel with a radiology workflow, in a parallel with a variation of the method 200 configured to triage a patient for treatment of the patient's condition, etc.), after one or more processes of a variation of the method 200 configured to triage a patient for treatment of the patient's condition has been performed, and/or at any other suitable times.

Figure 10:
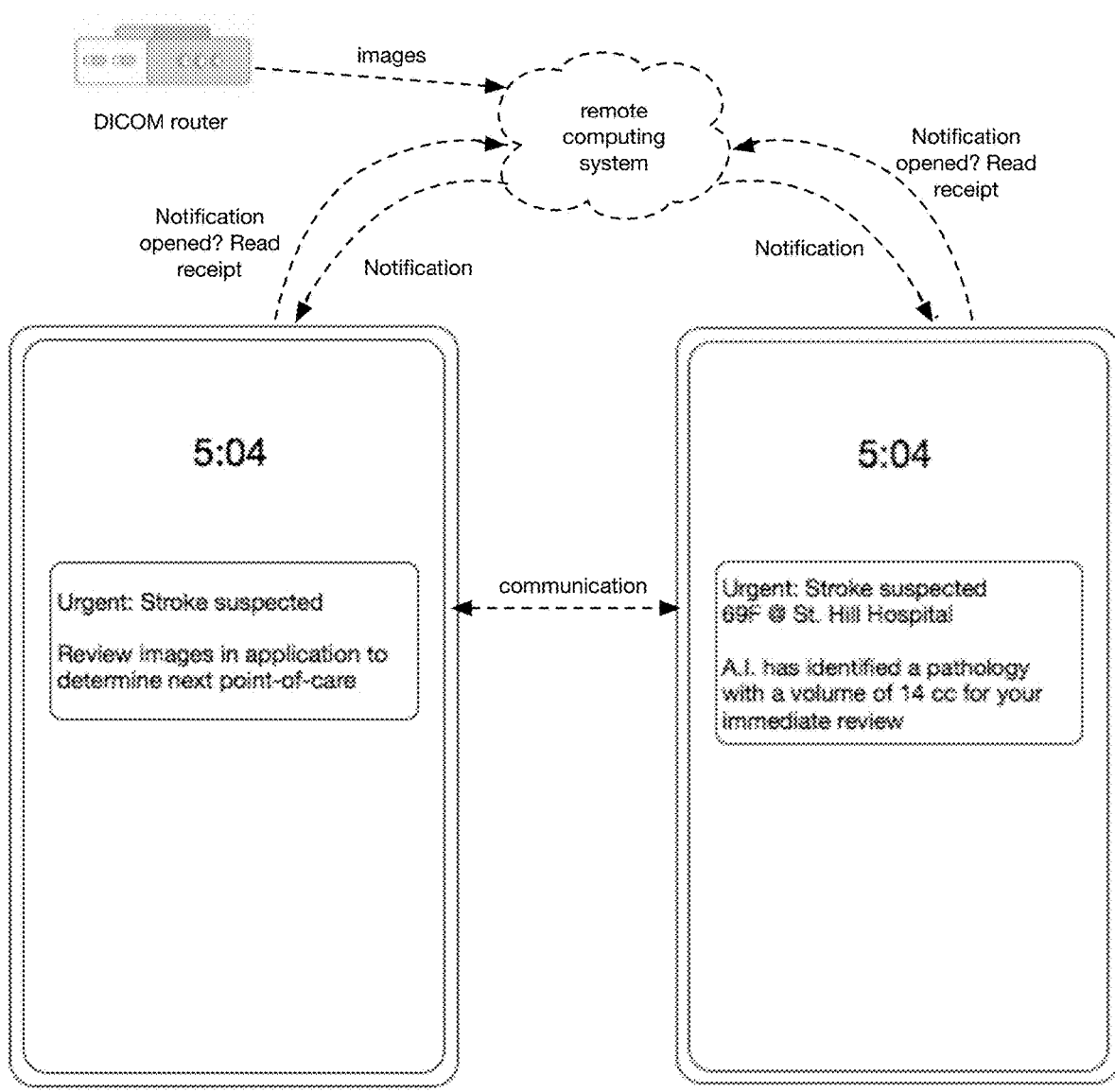
FIG. 10 depicts variations of applications on a first and second user device.

The method 200 can optionally include establishing communication between users, such as between any or all of: multiple healthcare workers (e.g., physicians, surgeons, etc.), multiple research coordinators (e.g., from the same clinical trial, from different clinical trials, etc.), a healthcare worker and a research coordinator (e.g., for the research coordinator to ask questions from the surgeon, as shown in FIG. 10, etc.), a research coordinator and a patient (e.g., to submit a consent form to the patient, to receive a consent form from the patient, etc.), a healthcare worker and a patient, and/or between any other suitable users and individuals.

The method 200 is preferably performed in response to a patient presenting at a first point of care. The first point of care can be an emergency setting (e.g., emergency room, ambulance, imaging center, etc.) or any suitable healthcare facility, such as those described previously. The patient is typically presenting with (or suspected to be presenting with) a time-sensitive condition, such as a neurovascular condition (e.g., stroke, ischemic stroke, occlusion, large vessel occlusion (LVO), intracerebral hemorrhage (ICH), thrombus, aneurysm, etc.), cardiac event or condition (e.g., cardiovascular condition, heart attack, etc.), trauma (e.g., acute trauma, blood loss, etc.), or any other time-sensitive (e.g., life-threatening) condition. In other variations, the method is performed for a patient presenting to a routine healthcare setting (e.g., non-emergency setting, clinic, imaging center, etc.), such as for routine testing, screening, diagnostics, imaging, clinic review, laboratory testing (e.g., blood tests), or for any other reason.

Any or all of the method can be performed using any number of deep learning (e.g., machine learning) modules. Each module can utilize one or more of: supervised learning (e.g., using logistic regression, using back propagation neural networks, using random forests, decision trees, etc.), unsupervised learning (e.g., using an Apriori algorithm, using K-means clustering), semi-supervised learning, reinforcement learning (e.g., using a Q-learning algorithm, using temporal difference learning), and any other suitable learning style. Each module of the plurality can implement any one or more of: a regression algorithm (e.g., ordinary least squares, logistic regression, stepwise regression, multivariate adaptive regression splines, locally estimated scatterplot smoothing, etc.), an instance-based method (e.g., k-nearest neighbor, learning vector quantization, self-organizing map, etc.), a regularization method (e.g., ridge regression, least absolute shrinkage and selection operator, elastic net, etc.), a decision tree learning method (e.g., classification and regression tree, iterative dichotomiser 3, C4.5, chi-squared automatic interaction detection, decision stump, random forest, multivariate adaptive regression splines, gradient boosting machines, etc.), a Bayesian method (e.g., naïve Bayes, averaged one-dependence estimators, Bayesian belief network, etc.), a kernel method (e.g., a support vector machine, a radial basis function, a linear discriminate analysis, etc.), a clustering method (e.g., k-means clustering, expectation maximization, etc.), an associated rule learning algorithm (e.g., an Apriori algorithm, an Eclat algorithm, etc.), an artificial neural network model (e.g., a Perceptron method, a back-propagation method, a Hopfield network method, a self-organizing map method, a learning vector quantization method, etc.), a deep learning algorithm (e.g., a restricted Boltzmann machine, a deep belief network method, a convolution network method, a stacked auto-encoder method, etc.), a dimensionality reduction method (e.g., principal component analysis, partial lest squares regression, Sammon mapping, multidimensional scaling, projection pursuit, etc.), an ensemble method (e.g., boosting, boostrapped aggregation, AdaBoost, stacked generalization, gradient boosting machine method, random forest method, etc.), and any suitable form of machine learning algorithm. Each module can additionally or alternatively be a: probabilistic module, heuristic module, deterministic module, or be any other suitable module leveraging any other suitable computation method, machine learning method, or combination thereof.

Each module can be validated, verified, reinforced, calibrated, or otherwise updated based on newly received, up-to-date measurements; past measurements recorded during the operating session; historic measurements recorded during past operating sessions; or be updated based on any other suitable data. Each module can be run or updated: once; at a predetermined frequency; every time the method is performed; every time an unanticipated measurement value is received; or at any other suitable frequency. The set of modules can be run or updated concurrently with one or more other modules, serially, at varying frequencies, or at any other suitable time. Each module can be validated, verified, reinforced, calibrated, or otherwise updated based on newly received, up-to-date data; past data or be updated based on any other suitable data. Each module can be run or updated: in response to determination of an actual result differing from an expected result; or at any other suitable frequency.

4.1 Method—Receiving Data from a First Point of Care S205

The method 200 can include receiving data (e.g., data packet) from a first point of care S205, which functions to collect data relevant to assessing a patient condition.

The data is preferably received at a router 110, wherein the router is in the form of a virtual machine operating on a computing system (e.g., computer, workstation, quality assurance (QA) workstation, reading workstation, PACS server, etc.) coupled to or part of an imaging modality (e.g., CT scanner, MRI scanner, etc.), or any other suitable router. Additionally or alternatively, data can be received at a remote computing system (e.g., from an imaging modality, from a database, a server such as a PACS server, an internet search, social media, etc.), or at any other suitable computing system (e.g., server) or storage site (e.g., database). In some variations, for instance, a subset of the data (e.g., image data) is received at the router while another subset of the data (e.g., patient information, patient history, etc.) is received at a remote computing system. In a specific example, the data subset received at the router is eventually transmitted to the remote computing system for analysis.

The first point of care is often a spoke facility (e.g., non-specialist facility) but can alternatively be a hub facility (e.g., specialist facility), mobile facility or transportation (e.g., ambulance), or any other suitable healthcare facility.

S205 is preferably performed in response to (e.g., after, in real time with, substantially in real time with, with a predetermined delay, with a delay of less than 10 seconds, with a delay of less than 1 minute, at the prompting of a medical professional, etc.) the data (e.g., each of a set of instances) being generated at the imaging modality. Additionally or alternatively, S205 can be performed in response to a set of multiple instances being generated by the imaging modality (e.g., after a partial series has been generated, after a full series has been generated, after a study has been generated, etc.), in response to a metadata tag being generated (e.g., for an instance, for a series, for a study, etc.), in response to a trigger (e.g., request for images), throughout the method (e.g., as a patient's medical records are accessed, as information is entered a server, as information is retrieved from a server, etc.), or at any other suitable time.

S205 can be performed a single time or multiple times (e.g., sequentially, at different times in the method, once patient condition has progressed, etc.). In one variations, each instance is received (e.g., at a router, at a remote computing system, etc.) individually as it is generated. In a second variation, a set of multiple instances (e.g., multiple images, full series, etc.) are received together (e.g., after a scan has completed, after a particular anatomical component has been imaged, etc.).

The router (e.g., virtual machine, virtual server, application running on the image sampling system or a computing system connected to the image sampling system, etc.) can be continuously 'listening' (e.g., operating in a scanning mode, receiving mode, coupled to or include a radio operating in a suitable mode, etc.) for information from the imaging modality, can receive information in response to prompting of a healthcare facility worker, in response to a particular scan type being initiated (e.g., in response to a head CTA scan being initiated), or in response to any other suitable trigger.

Image data is preferably received at the router (e.g., directly, indirectly, etc.) from the imaging modality (e.g., scanner) at which the data was generated. Additionally or alternatively, image data or any other data can be received from any computing system associated with the healthcare facility's PACS server, any DICOM-compatible devices such as a DICOM router, or any other suitable computing system. The image data is preferably in the DICOM format but can additionally or alternatively include any other data format.

In addition to or alternative to image data, the data can include blood data, electronic medical record (EMR) data, unstructured EMR data, health level 7 (HL7) data, HL7 messages, clinical notes, or any other suitable data related to a patient's medical state, condition, or medical history.

The data preferably includes a set of one or more instances (e.g., images), which can be unorganized, organized (e.g., into a series, into a study, a sequential set of instances based on instance creation time, acquisition time, image position, instance number, unique identification (UID), other acquisition parameters or metadata tags, anatomical feature or location within body, etc.), complete, incomplete, randomly arranged, or otherwise arranged.

Each instance preferably includes (e.g., is tagged with) a set of metadata associated with the image dataset, such as, but not limited to: one or more patient identifiers (e.g., name, identification number, UID, etc.), patient demographic information (e.g., age, race, sex, etc.), reason for presentation (e.g. presenting symptoms, medical severity score, etc.), patient history (e.g., prior scans, prior diagnosis, prior medical encounters, etc.), medical record (e.g. history of present illness, past medical history, allergies, medications, family history, social history, etc.), scan information, scan time, scan type (e.g., anatomical region being scanned, scanning modality, scanner identifier, etc.), number of images in scan, parameters related to scan acquisition (e.g., timestamps, dosage, gurney position, scanning protocol, contrast bolus protocol, etc.), or any other suitable information.

In some variations, any or all of the data (e.g., image data) is tagged with metadata associated with the standard DICOM protocol.

In some variations, one or more tags is generated and/or applied to the data after the data is generated at an imaging modality. In some examples, the tag is an identifier associated with the $1^{st}$ point of care (e.g., $1^{st}$ point of care location, imaging modality identifier, etc.), which can be retrieved by a $2^{nd}$ point of care in order to locate the patient (e.g., to enable a quick transfer of the patient, to inform a specialist of who to contact or where to reach the patient, etc.).

Additionally or alternatively, image data can be received without associated metadata (e.g., metadata identified later in the method, dataset privately tagged later with metadata later in the method, etc.)

Data can be received (e.g., at the router) through a wired connection (e.g., local area network (LAN) connection), wireless connection, or through any combination of connections and information pathways.

In some variations, images are generated at an imaging modality (e.g., CT scanner) in response to a standard stroke protocol.

4.2 Method—Transmitting Data to a Remote Computing System S208

The method can include transmitting data to remote computing system (e.g., remote server, PACS server, etc.) S208, which functions to enable remote processing of the data, robust process, or fast processing (e.g., faster than analysis done in clinical workflow, faster than done in a standard radiology workflow, processing less than 20 minutes, less than 10 minutes, less than 7 minutes, etc.) of the dataset.

The data (e.g., image data, image data and metadata, etc.) is preferably transmitted to a remote computing system from a router (e.g., virtual machine operating on a scanner) connected to a computing system (e.g., scanner, workstation, PACS server, etc.) associated with a healthcare facility, further preferably where the patient first presents (e.g., $1^{st}$ point of care), but can additionally or alternatively be transmitted from any healthcare facility, computing system, or storage site (e.g., database).

Each instance (e.g., image) of the dataset (e.g., image dataset) is preferably sent individually as it is generated at an imaging modality and/or received at a router, but additionally or alternatively, multiple instances can be sent together after a predetermined set (e.g., series, study, etc.) has been generated, after a predetermined interval of time has passed (e.g., instances sent every 10 seconds), upon the prompting of a medical professional, or at any other suitable time. Further additionally or alternatively, the order in which instances are sent to a remote computing system can depend one or more properties of those instances (e.g., metadata). S208 can be performed a single time or multiple times (e.g., after each instance is generated).

S208 can include transmitting all of the dataset (e.g., image dataset and metadata), a portion of the dataset (e.g., only image dataset, subset of image dataset and metadata, etc.), or any other information or additional information (e.g., supplementary information such as supplementary user information).

The data is preferably transmitted through a secure channel, further preferably through a channel providing error correction (e.g., over TCP/IP stack of 1st point of care), but can alternatively be sent through any suitable channel.

S208 can include any number of suitable sub-steps performed prior to or during the transmitting of data to the remote computing system. These sub-steps can include any or all of: encrypting any or all of the dataset (e.g., patient information) prior to transmitting to the remote computing system, removing information (e.g., sensitive information), supplementing the dataset with additional information (e.g., supplementary patient information, supplemental series of a study, etc.), compressing any or all of the dataset, or performing any other suitable process.

4.3 Method—Preparing a Data Packet for Analysis S210

The method 200 preferably includes preparing a data packet S210 for analysis, which can function to decrease the time required to analyze the data packet, eliminate irrelevant data packets from further analysis, remove irrelevant data from a data packet (e.g., irrelevant anatomical regions), or perform any other suitable function.

Preparing a data packet for analysis can include organizing a set of instances (e.g., images, slices, scans, etc.), preferably into a series, but additionally or alternatively into a study, or any other suitable grouping of images. The organization is preferably performed in response to generating a set of instances (e.g., at an imaging modality), but can additionally or alternatively be performed in response to receiving a set of instances at a location (e.g., router, remote computing system, server such as a PACS server, etc.), at the request of an individual (e.g., healthcare worker), in response to a trigger, or at any other suitable time. Additionally or alternatively, the set of instances can be performed multiple times throughout the method (e.g., based on the same organization scheme/metadata, based on different organization schemes/metadata, etc.). The organization can be done at a remote computing system, a healthcare facility computing system, a virtual machine (e.g., operating on a healthcare facility computing system), or at any other suitable computing or processing system, physical or virtual, local (e.g., at a healthcare facility) or remote. The set of images are preferably organized based on a set of metadata (e.g., metadata tags, conventional DICOM metadata tags, etc.), but can additionally or alternatively be organized in any other suitable way (e.g., organized by time of receipt, ranked order of importance, etc.). In one variation, a set of images are organized into a series based on a set of metadata, wherein the series is formed from images having metadata corresponding to any or all of the following: images taken in an axial series, images each corresponding to a thin slice (e.g., 0.625 millimeters (mm) or thinner), no missing slices (e.g., no jump in a slice number between adjacent images), a consistent pixel spacing across the series, and aligned instance numbers and positions. Additionally or alternatively, any other metadata can be used to determine the series.

In some variations, the method includes excluding a data packet (e.g., set of instances) from further processing if one or more of a set of metadata are not satisfied, such as, but not limited to, the metadata listed above.

Preparing a data packet can additionally or alternatively include extraction of data, such as one or more materials or features in the set of instances (e.g., series), which can function to reduce the computational cost and time of one or more remaining steps of the method (e.g., by removing irrelevant features in one or more instances). This can include any or all of pixel-based methods, voxel-based methods, comparing non-image data (e.g., blood test results) with one or more predetermined thresholds, or any other suitable method(s). The data is preferably extracted after the data packet has been organized (e.g., into a series), but can additionally or alternatively be performed in absence of the data packet being organized, in response to a trigger, in multiple steps and/or at multiple times throughout the method (e.g., extract a first material and then a subset of that material), or at any other point during the method. The data is preferably extracted at a remote computing system (e.g., single computing system), but can additionally or alternatively be performed at any suitable computing system. Data can be extracted based on any or all of: HU value thresholding, photomasks, dilation, erosion, or any other technique.

In some variations, such as those involving patients presenting with a stroke symptom or condition (e.g., large vessel occlusion), this can include extracting portions of the image corresponding to soft matter (e.g., brain tissue, cerebral fluid, blood, etc.) and/or removing portions of the image correspond to hard matter (e.g., bone, skull, etc.). This is preferably done by leveraging the fact that soft matter corresponds to a set of low Hounsfield Unit (HU) values, which is differentiated from any surrounding hard matter (e.g., bone, skull), which corresponds to a set of high HU values.

In a specific example, a bone mask is determined and defined as a set of voxels having an HU value above a predetermined threshold (e.g., 750 HU, 700 HU, 800 HU, between 600 HU and 900 HU, etc.). The bone mask is then dilated with a series of kernels of increasing size until it completely encloses a set of voxels of low HU values (e.g., less than the predetermined threshold), thereby defining a soft matter mask. The soft matter mask is dilated to compensate for the dilation of the bone mask. If the process of defining the soft matter mask fails, this can indicate that the skull has undergone a craniotomy, which in some cases can be used in determining a diagnosis, informing a contact or second point of care, or in any other point in the method. Once the soft matter mask is dilated, the mask can then be applied to the set of instances (e.g., organized set of instances, series, etc.), and the HU value of voxels outside of the mask is set to zero.

Preparing a data packet preferably includes evaluating one or more exclusion criteria in the set of instances, which can function to verify that a set of instances is relevant for evaluation in the rest of the method, save time and/or resources by eliminating irrelevant sets of instances, route a set of instances corresponding to one or more exclusion criteria to another workflow in a healthcare facility, or perform any other suitable function. Alternatively, the method can partially or fully process all sets of instances. The exclusion criteria are preferably applied after data has been extracted (e.g., to reduce processing time), but can additionally or alternatively be performed prior to or in absence of the extraction of data, multiple times throughout the method (e.g., different exclusion criteria applied depending on the degree of processing of the set of instances), or at any other suitable time during the method. Evaluating data for exclusion criteria is preferably performed at the remote computing system, but can additionally or alternatively be performed at any other computing system.

The exclusion criteria preferably include any or all of: the presence of an artifact in one or more of the set of instances (e.g., metallic artifact, aneurysm clip, etc.), improper timing at which the set of instances were taken at an imaging modality (e.g., premature timing, improper timing of a bolus, etc.), one or more incomplete regions (e.g., features, anatomical features, etc.) in the set of instances (e.g., incomplete skull, incomplete vessel, incomplete soft matter region, etc.), an incorrect scan type or body part (e.g., non-head CT scan, non-contrast CT scan, etc.), poor image quality (e.g., blurry images, low contrast, etc.), movement of patient during scan, or any other suitable exclusion criteria.

In one variation, a set of instances (e.g., images, series, etc.) are evaluated to determine if an artifact is present, wherein the set of instances is excluded from further steps in the method if an artifact is found. In a specific example, the method includes inspecting the HU values of voxels in a soft matter mask, wherein voxels having a value above a predetermined threshold (e.g., 3000 HU, between 2000 and 4000 HU, etc.) are determined to be a metallic artifact (e.g., aneurysm clip).

In a second variation, a set of instances are evaluated to determine if bad bolus timing occurred during the generation of the set of instances at an imaging modality. In a specific example, a soft matter mask is eroded with a wide kernel, which functions to remove potential high HU voxels due to a partial volume effect caused by bone voxels. The HU values of the voxels within the eroded mask are inspected and the number of voxels having a value above a predetermined threshold (e.g., 100 HU, between 10 and 200 HU, etc.) can be counted (e.g., correlated to a volume) and used to determine if the timing of the scan was premature. If the timing of the scan was premature, the contrast (e.g., contrast agent, dye, etc.) in a contrast CT scan, for instance, should not be visible within the soft matter and typical HU values of the voxels will be below the predetermined threshold (e.g., less than 100 HU). If the total volume of voxels having a value greater than the predetermined threshold is less than a predetermined volume threshold (e.g., 10 cc, 20 cc, 5 cc, etc.), the set of instances (e.g., series) can be rejected based on bad bolus timing (e.g., premature scan). In some specific examples, this process is selectively applied (e.g., only to an anterior part of the soft matter to avoid mistaking of calcifications of the choroid plexus or pineal gland as contrast).

In a third variation, a set of instances are evaluated to determine if an anatomical feature is incomplete or missing from the set of instances. In a specific example, the set of instances are evaluated to determine if a complete or nearly complete (e.g., area or volume above a predetermined threshold) skull is present. This can include inspecting a total area of cerebral soft matter in a particular slice (e.g., top slice), wherein if the total area exceeds a predetermined threshold (e.g., 80 centimeters squared, 90 centimeters squared, between 70 and 100 centimeters squared, etc.), the set of instances is excluded as being incomplete.

In a fourth variation, a set of instances are evaluated to determine if the instances align with one or more criteria associated with a clinical trial. In specific examples, a set of one or more parameters (e.g., volume of an ICH, hematoma volume, volume of affected brain tissue, length of a vessel occlusion, etc.) determined based on the images and/or patient information is compared with a set of inclusion and exclusion criteria associated with a clinical trial.

S210 can include one or more registration steps (e.g., image registration steps), wherein any or all of the set of instances (e.g., soft matter extracted from set of instances) are registered to a reference set of instances (e.g., reference series), which can function to align, scale, calibrate, or otherwise adjust the set of instances. The registration step is preferably performed in response to a data packet being filtered through a set of exclusion criteria, but can additionally or alternatively be performed prior to or in absence of the filtering, multiple times throughout the method, or at any other suitable time.

The registration step can be intensity-based, feature-based, or any other type or registration and can include any or all of point-mapping, feature-mapping, or any other suitable process. The reference set of instances is preferably determined from a training set but can alternatively be determined from any suitable dataset, computer-generated, or otherwise determined. The reference series can be selected for any or all of orientation, size, three-dimensional positioning, clarity, contrast, or any other feature. In one variation, a references series is selected from a training set, wherein the reference series is selected based on a feature parameter (e.g., largest feature size such as largest skull, smallest feature size, etc.) and/or a degree of alignment (e.g., maximal alignment, alignment above a predetermined threshold, etc.). Additionally or alternatively, any other criteria can be used to determine the reference series, the reference series can be randomly selected, formed from aggregating multiple sets of instances (e.g., multiple patient series), or determined in any other suitable way. In some variations, the registration is performed with one or more particular software packages (e.g., SimpleElastix). In a specific example, the registration is performed through affine registration (e.g., in SimpleElastix) with a set of predetermined (e.g., default) parameters and iterations (e.g., 4096 iterations, between 3000 and 5000 iterations, above 1000 iterations, above 100 iterations, etc.) in each registration step.

In one variation, a skull-stripped series (e.g., series having soft matter extracted) is registered to a reference series chosen from a training set, wherein the reference series was chosen based on it having a large skull size and a high level of alignment among its set of instances.

In a second variation, a skull-stripped series is registered to a reference series formed from an aggregated set of series.

Additionally or alternatively, preparing the data packet can include any other suitable steps.

4.4 Method—Determining a Parameter Associated with the Data Packet S220

Figure 4:
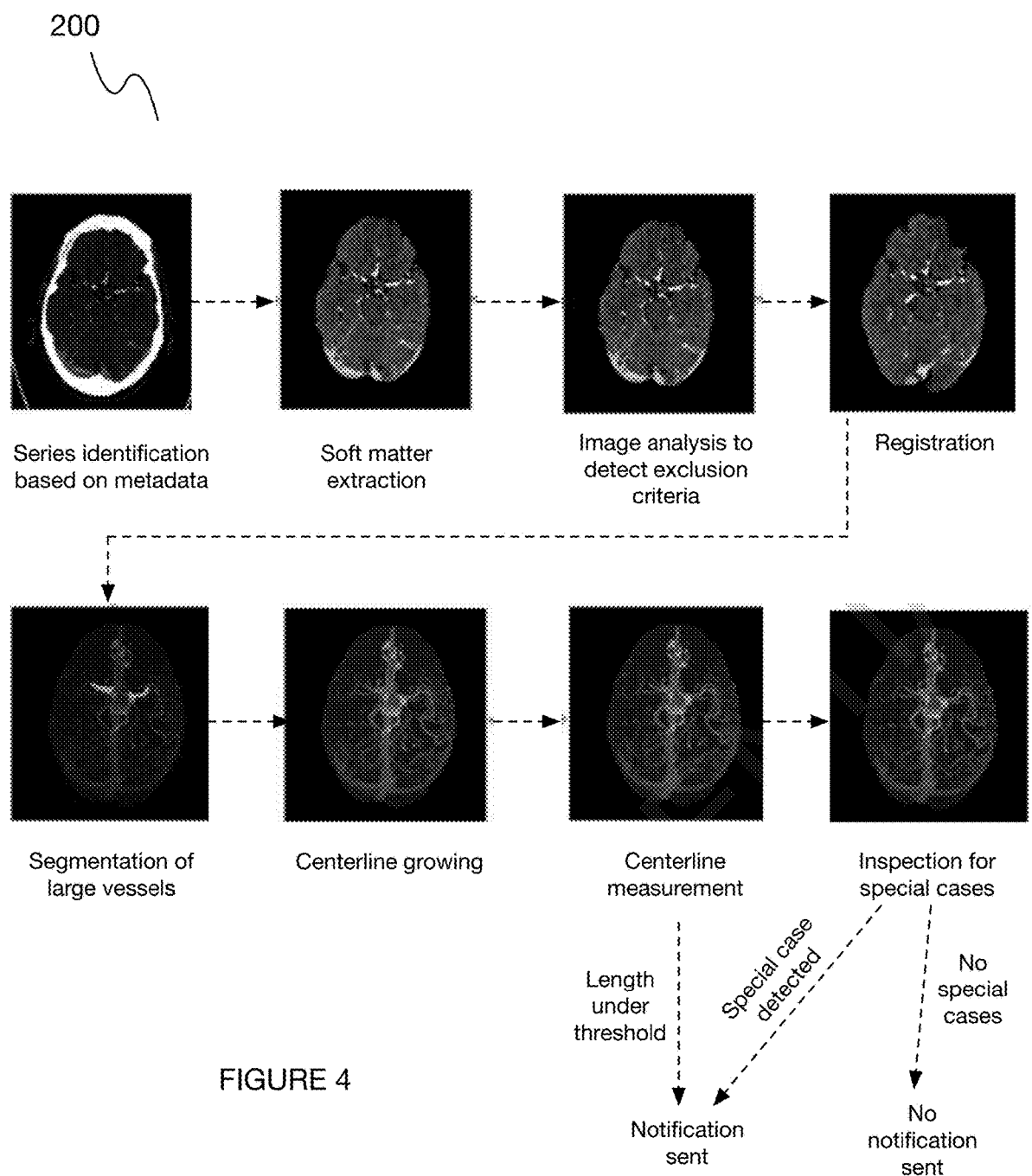
FIG. 4 depicts a variation of determining a patient condition during a method for computer-aided triage.

The method 200 preferably includes determining a parameter associated with the data packet S220 (e.g., as shown in FIG. 4), which functions to assess a patient condition which subsequently informs the rest of the method 200. Additionally or alternatively, S220 can function to reduce the time to transfer a patient to a second point of care, halt progression of the condition, or perform any other suitable function. S220 is preferably fully performed at a remote computing system (e.g., remote server, cloud-based server, etc.), further preferably a remote computing system having a graphics processing unit (GPU), but can additionally or alternatively be partially performed at any suitable remote computing system, be partially or fully performed at a local computing system (e.g., workstation), server (e.g., PACS server), at a processor of a user device, or at any other system. S220 is preferably partially or fully performed using software including one or more algorithms, further preferably one or more multi-step algorithms containing steps that are either trained (e.g., trained through machine learning, trained through deep learning, continuously trained, etc.) or non-trained (e.g., rule-based image processing algorithms or heuristics). Additionally or alternatively, any software can be implemented.

S220 preferably includes identifying (e.g., locate, isolate, measure, quantify, etc.) an anatomical feature S222 within the data packet, further preferably within a registered series of images but alternatively within any suitable image dataset. This can be performed through any number of computer vision techniques, such as object recognition, object identification, object detection, or any other form of image analysis. In some variations, the anatomical feature analysis is performed at least partially through image segmentation, wherein the segmentation includes any or all of: thresholding, clustering methods, dual clustering methods, compression-based methods, histogram-based methods, region-growing methods, partial differential equation-based methods, variational methods, graph partitioning methods, watershed transformations, model based segmentation, multi-scale segmentation, semi-automatic segmentation, trainable segmentation, or any suitable form of segmentation. The method can additionally or alternatively include any number of segmentation post-processing steps, such as thresholding, connectivity analyses, or any other processing. The segmentation is preferably performed with a convolutional neural network (CNN), further preferably feed-forward deep CNN (e.g., using three-dimensional convolutions, two-dimensional convolutions, etc.), but can additionally or alternatively be performed using any suitable algorithm or process.

In variations, such as those involving stroke (e.g., ischemic stroke, LVO, etc.), the anatomical feature can be one or more blood vessels (e.g., arteries, large paired arteries, etc.), such as the internal carotid artery (ICA) (e.g., terminal ICA (t-ICA)), middle cerebral artery (MCA), or any other vessel or other anatomical feature. Additionally or alternatively, the anatomical feature can be soft matter (e.g., brain tissue), hard matter (e.g., bone), or any other feature. In other variations, the anatomical feature can be a part of the heart (e.g., vessel, artery, lobe, etc.), a bone (e.g., fractured bone), or any other part of the body.

S222 is preferably performed after the image data (e.g., series) has been registered to a reference series but can additionally or alternatively be performed prior to or in absence of a registration step, in response to a trigger, multiple times throughout the method, or at any other suitable time.

In some variations, such as in the case of a patient presenting with a stroke (e.g., ischemic stroke, vessel occlusion, LVO, etc.), a large vessel region (e.g., t-ICA and MCA-M1 segments) is segmented.

In other variations, an anatomical feature (e.g., thrombus, aneurysm, etc.) within a vessel is identified. In a specific example, for instance, a clot is segmented. The segmented clot can be assessed (e.g., using other processes of the method 200) to determine, for instance, one or more parameters (e.g., size, length, volume, etc.) of the clot and compare the one or more parameters with one or more predetermined thresholds (e.g., anatomical thresholds or parameters).

In yet other variations, an anatomical feature outside of the brain vasculature, such as a tumor, tissue region (e.g., infarcted tissue), swelled region, or any other suitable feature can be identified.

The method further preferably includes determining a parameter associated with the anatomical feature S224, which functions to assess (e.g., quantify) the anatomical feature. S224 is preferably performed using one or more computer vision/image processing techniques, which can, for instance, include any or all of: centerline extraction, centerline extension, a distance measurement (e.g., between two ends of a feature, between two ends of a centerline, etc.), size measurement (e.g., length, width, thickness, volume, estimated mass, etc.), direction or orientation measurement, intensity measurement, or any suitable measurement can be performed.

In some variations of the method, such as those implemented for a suspected vessel occlusion (e.g., LVO), a centerline length is determined through a centerline extension process. This can be performed through any or all of: binary masks, voxel thresholding, one or more trimming steps, a three-dimensional parallel thinning algorithm, or any other process. In an example, for instance, the centerline extension process includes extending a large vessel centerline based on a set of HU values of one or more voxels (e.g., end voxels, voxels adjacent centerline ends of a large vessel occlusion, middle voxels, voxels having HU values above a predetermined threshold, voxels having HU values below a predetermined threshold, voxels having HU values within a predetermined range, etc.) to generate an extended centerline. A parameter (e.g., centerline length) can then be calculated, for instance, from the extended centerline.

In one specific example, a centerline length is determined for a vessel segmentation, such as a vessel segmentation (e.g., probabilistic vessel segmentation) described previously. Determining the centerline length can include any or all of: conversion of image data to a mask (e.g., binary mask), thresholding, converting the mask to a centerline (e.g., through a three-dimensional parallel thinning algorithm), growing the centerline (e.g., based on a predetermined set of criteria), fusing of centerline skeletons, preserving one or more conditions or features (e.g., topological, geometrical, etc.), pre-processing, post-processing, or any other suitable process.

In some variations, an algorithm (e.g., for determining a centerline length) is determined to optimize for speed. Additionally or alternatively, an algorithm can be selected to optimize for noise sensitivity or any other suitable feature.

In some variations, the process is repeated until one or more of a set of conditions are met. These conditions can include, for instance, that a parameter (e.g., distance, length, volume, area, voxel value, pixel value, etc.) is related in a predetermined way (e.g., within, above, below, etc.) a decision threshold, that the process has been repeated for a predetermined number of times (e.g., 5 times, 10 times, etc.), or any other suitable criteria.

In some variations, a trimming step is performed at the end of each iteration to remove irrelevant features. In a specific example, for instance, a trimming step is performed to remove (e.g., clean) short branches which do not represent large vessels.

The method preferably includes comparing the parameter with a threshold S226, which functions to determine (or alternatively rule out) a suspected condition. The condition typically refers to a hypothesized patient condition or diagnosis (e.g., LVO, aneurysm, stroke, etc.) but can additionally or alternatively include a severity (e.g., based on a predetermined severity scale), an urgency, or any other characteristic.

S226 is preferably performed after and in response to S224 but can additionally or alternatively be performed at any suitable time in the method. The threshold (e.g., threshold value) is preferably determined based on clinical data and/or anatomical data, such as a geometrical feature, size (e.g., average size, aggregated size, random size, optimal size, largest size, etc.) of an anatomical feature, intensity of a feature (e.g., contrast-filled vessel), or any other suitable characteristic. In some variations, the threshold is determined based on one or more training sets of data, wherein the training sets are used to develop one or more algorithms used in the method.

S226 can optionally include determining the threshold. In some variations, the threshold is chosen to be greater than the value (e.g., average value, highest value, upper limit of a standard range, optimal value, etc.) of the corresponding anatomical feature, which can function to increase the sensitivity of the determination of a patient condition, increase the number of false positives (e.g., when false positives have a negligible effect on a workflow), affect a specificity (e.g., decrease) of the determination of a patient condition, or perform any other suitable function. In one example, for instance, the threshold against which a centerline length of a vessel (e.g., t-ICA plus proximal MCA-M1) is compared is chosen to be larger than the corresponding anatomical length (e.g., average total length of t-ICA and proximal MCA-M1, maximum total length of t-ICA and proximal MCA-M1, etc.). Alternatively, the threshold can be chosen to be smaller, approximately average, optimal, or otherwise comparable to an anatomical feature.

In some variations of the method, such as those implemented in patients presenting with an LVO, a computed centerline length is determined and compared with a threshold centerline length (e.g., larger than average centerline length). If the computed centerline length is less than the threshold, an LVO is suspected. If the centerline length is greater than the threshold, no LVO is suspected. This can be used to determine whether or not the patient should be transferred to a specialist, to inform a healthcare worker at a first point of care, or for any other suitable purpose. In a specific example, a total length of a large vessel region (e.g., t-ICA and proximal MCA-M1) was determined to have a particular value (e.g., 50 mm, 53 mm, between 50 mm and 60 mm, less than 60 mm, less than 70 mm, etc.), and a threshold length was chosen to be larger (e.g., 60 mm, greater than 60 mm, etc.) than that value to optimize for true positives.

In some variations, S226 can include performing a process during a training step, wherein the process is used to determine on optimal threshold. In a specific example, for instance, one or more receiver operating characteristic (ROC) analyses are performed to investigate the performance of an algorithm for a variety of potential thresholds, thereby determining an optimal threshold (e.g., elbow point).

In one variation, user-calibrated distance thresholds are used to determine if the distance between the proximal and distal parts of an extracted centerline is indicative of (e.g., within a range of thresholds) an LVO. In a specific example, user-calibrated intensity thresholds are used to determine if a partial LVO is present.

The method 200 can further include testing for a set of special cases, which can function to increase the probability that a true positive is detected during the method. The special cases (special conditions) typically correspond to less common anatomical or clinical configurations of the condition (e.g., LVO) but can additionally or alternatively correspond to a degraded image quality of a set of instances, or any other suitable event. In some variations of patients presenting with an LVO, for instance, an LVO can be present even when the centerline length is above the predetermined threshold. This can include investigating one or more features of the anatomical feature and its parameters, such as an orientation of an anatomical feature (e.g., orientation of vessel centerline), geometrical feature (e.g., width of a vessel), or any other suitable feature indicative of a special case.

In one example, the method includes checking for a partial occlusion. In such cases, contrast can still partially fill the vessel, so a centerline extension can succeed and result in a centerline length above the predetermined threshold. Checking for a partial occlusion can include comparing the HU value of the centerline voxels to the HU value of a set of immediately adjacent voxels. If a difference of greater than a predetermined threshold value (e.g., 200 HU) is seen between the voxel groups, an LVO can be detected and/or indicated in future steps.

In a second example, the method includes checking for a fetal origin posterior cerebral artery (PCA), which corresponds to an LVO occurring immediately after a fetal origin PCA bifurcation, as the centerline extension extends into the PCA instead of into the MCA. This can be detected by inspecting an orientation of the centerline extension, and if the centerline extends posteriorly to a greater degree than it extends distally, an LVO can be detected and/or indicated in future steps.

Additionally or alternatively, any other special cases can be examined in any suitable way.

4.5 Method—Determining a Treatment Option S230

The method can include determining a treatment option S230, preferably in the event that a condition is detected (e.g., based on a comparison with a threshold) but can additionally or alternatively determine a treatment option when a condition is not detected, when an analysis is inconclusive, or in any suitable scenario. S230 can function to initiate the transfer of a patient to a $2^{nd}$ point of care (e.g., specialist facility), initiate the transfer of a specialist to a $1^{st}$ point of care, or initiate treatment of a patient (e.g., mechanical thrombectomy) within the $1^{st}$ point of care, or perform any other suitable function. In some variations, the treatment option is a $2^{nd}$ point of care, wherein it is determined (e.g., suggested, assigned, etc.) that the patient should be treated at the $2^{nd}$ point of care. Additionally or alternatively, the treatment option can be a procedure (e.g., surgical procedure, mechanical thrombectomy, placement of an aneurysm coil, placement of a stent, retrieval of a thrombus, etc.), treatment (e.g., tissue plasminogen activator (TPA), pain killer, blood thinner, etc.), recovery plan (e.g., physical therapy, speech therapy, etc.), or any other suitable treatment.

The treatment is preferably determined based on a comparison between a parameter determined from the data packet and a threshold, but can additionally or alternatively be determined based on additional data, such as patient information (e.g., demographic information, patient history, patient treatment preferences, etc.), input from one or more individuals (e.g., power of attorney, attending physician, emergency physician, etc.), or any other suitable information.

S230 is preferably at least partially performed with software operating at the remote computing system (e.g., remote server) but can additionally or alternatively be performed at a remote computing system separate from a previous remote computing system, a local computing system (e.g., local server, virtual machine coupled to healthcare facility server, computing system connected to a PACS server), or at any other location.

S230 is preferably performed after a patient condition has been determined during the method 200. Additionally or alternatively, S230 can be performed after a patient condition has been determined in an alternative workflow (e.g., at the $1^{st}$ point of care, at a radiologist workstation during a standard radiology workflow, in the case of a false negative, etc.), prior to or absent the determination of a patient condition (e.g., based on an input from a healthcare worker at the remote computing system, when patient is admitted to $1^{st}$ point of care, etc.), multiple times throughout the method (e.g., after a first treatment option fails, after a first specialist is unresponsive, such as after a threshold amount of time, such as 30 seconds, 1 minute, 2 minutes, etc.), or at any other time during the method.

S230 preferably determines a treatment option with a lookup table located in a database accessible at remote computing system (e.g., cloud-computing system). Additionally or alternatively, a lookup table can be stored at a healthcare facility computing system (e.g., PACS server), in storage at a user device, or at any other location.

In other variations, the treatment option can be determined by an algorithm (e.g., predictive algorithm, trained algorithm, etc.), an individual (e.g., specialist), a decision support tool, a set of criteria (e.g., qualification criteria for a clinical trial), or through any other process or tool.

The lookup table preferably correlates a $2^{nd}$ point-of-care (e.g., healthcare facility, hub, physician, specialist, neuro-interventionist, etc.), further preferably a specialist or contact (e.g., administrative worker, emergency room physician, etc.), with a patient condition (e.g., presence of an LVO, presence of a pathology, severity, etc.), but can additionally or alternatively correlate any treatment option with the patient condition. The lookup table can further additionally or alternatively correlate a treatment option with supplementary information (e.g., patient history, demographic information, heuristic information, etc.).

The contact (e.g., healthcare provider, neuro-interventional specialist, etc.) is preferably a healthcare worker, but can additionally or alternatively be any individual associated with the treatment of the patient and/or be associated with any healthcare facility (e.g., prior healthcare facility of patient, current healthcare facility, recommended healthcare facility) related to the patient. The contact is further preferably a specialist (e.g., neuro-interventional specialist, neurosurgeon, neurovascular surgeon, general surgeon, cardiac specialist, etc.) but can additionally or alternatively include an administrative worker associated with a specialist, multiple points of contact (e.g., ranked order, group, etc.), or any other suitable individual or group of individuals. The contact is preferably associated with a hub facility, wherein the hub facility is determined as an option for second point of care, but can additionally or alternatively be associated with a spoke facility (e.g., current facility, future facility option, etc.), an individual with a relation to the patient (e.g., family member, employer, friend, acquaintance, emergency contact, etc.), a research facility (e.g., research institution, national laboratory, academic institution, etc.) such as a research facility involved in a clinical trial, or any other suitable individual or entity (e.g., employer, insurance company, etc.). Additionally or alternatively, the contact can be an individual associated with a clinical trial (e.g., PI, research nurse, doctor, student, researcher, etc.).

The lookup table is preferably determined based on multiple types of information, such as, but not limited to: location information (e.g., location of a $1^{st}$ point of care, location of a $2^{nd}$ point of care, distance between points of care, etc.), temporal information (e.g., time of transit between points of care, time passed since patient presented at $1^{st}$ point of care, etc.), features of condition (e.g., size of occlusion, severity of condition, etc.), patient demographics (e.g., age, general health, history, etc.), specialist information (e.g., schedule, on-call times, historic response time, skill level, years of experience, specialty procedures, historic success or procedures, etc.), healthcare facility information (e.g., current number of patients, available beds, available machines, etc.), but can additionally or alternatively be determined based on a single type of information or in any other suitable way. Information can be actual, estimated, predicted, or otherwise determined or collected.

A location can be a set of geographic coordinates (e.g., latitude and longitude), a place name (e.g., county, city, landmark, intersection, etc.), a physical street address, distance from a given location, presence within a specified radius from a given location, a graphical depiction on a map, or any other suitable location expression. The location can be determined based on GPS coordinates provided by a device, triangulation between mobile phone towers and public masts (e.g., assistive GPS), Wi-Fi connection location, WHOIS performed on IP address or MAC address, GSM/CDMA cell IDs, location information self-reported by a user, or determined in any other suitable manner.

In some variations, the method 200 includes transmitting information (e.g., patient condition, data determined from analysis, optimal set of instances, series, data packet, etc.) to the computing system associated with the lookup table.

S230 can optionally additionally or alternatively include associating a patient with a clinical trial (e.g., based on a set of inclusion criteria, based on a set of exclusion criteria, etc.), which can function to efficiently and accurately recruit suitable patients for clinical trials. Associating a patient with a clinical trial can include any or all of: detecting a match (e.g., with at least a predetermined confidence threshold) and/or an overlap between a condition of the patient and a condition being examined and/or treated in the clinical trial, determining the satisfaction of a set of predetermined clinical trial criteria, determining an agreement between demographic information of the patient and requirements of the clinical trial, determining an agreement between environmental information (e.g., place of residence) of the patient and requirements of the clinical trial, and/or any other suitable processes and criteria. Associating the patient with the clinical trial can occur at any or all of the following: in parallel with determining a treatment option, after determining a treatment option (e.g., such that treatment of the patient occurs first), in place of determining a treatment option, and/or at any other suitable time(s). Additionally or alternatively, associating the patient with a clinical trial can occur in any other suitable way.

4.6 Method—Preparing a Data Packet for Transfer S240

The method 200 can include preparing a data packet for transfer, which can function to produce a compressed data packet, partially or fully anonymize a data packet (e.g., to comply with patient privacy guidelines, to comply with Health Insurance Portability and Accountability Act (HIPAA) regulations, to comply with General Data Protection Regulation (GDRP) protocols, etc.), minimize the time to transfer a data packet, or perform any other suitable function. Additionally or alternatively, any or all of a data packet previously described can be transferred.

The data packet is preferably transferred (e.g., once when data packet is generated, after a predetermined delay, etc.) to a contact, further preferably a specialist (e.g., associated with a $2^{nd}$ point of care, located at the $1^{st}$ point of care, etc.), but can additionally or alternatively be sent to another healthcare facility worker (e.g., at $1^{st}$ point of care, radiologist, etc.), an individual (e.g., relative, patient, etc.), a healthcare facility computing system (e.g., workstation), a server or database (e.g., PACS server), or to any other suitable location.

S240 preferably includes compressing a set of images (e.g., series), but can additionally or alternatively leave the set of images uncompressed, compress a partial set of images (e.g., a subset depicting the condition), or compress any other part of a data packet. Compressing the data packet functions to enable the data packet to be sent to, received at, and viewed on a user device, such as a mobile device. Compressing the data packet can include any or all of: removing a particular image region (e.g., region corresponding to air, region corresponding to hard matter, region without contrast dye, irrelevant anatomical region, etc.), thresholding of voxel values (e.g., all values below a predetermined threshold are set to a fixed value, all values above a predetermined threshold are set to a fixed value, all values below −500 HU are set to −500, all voxel values corresponding to a particular region are set to a fixed value, all voxels corresponding to air are set to a predetermined fixed value, etc.), reducing a size of each image (e.g., scale image size by factor of 0.9, scale image size by factor of 0.7, scale image size by factor of 0.5, scale image size by a factor between 0.1 and 0.9, reduce image size by a factor of 4, etc.), or through any other compression method.

In one variation, the reduction in size of a set of images can be determined based on one or more memory constraints of the receiving device (e.g., user device, mobile device, etc.).

In some variations, such as those involving a patient presenting with a brain condition (e.g., LVO), the images taken at an imaging modality (e.g., CT scanner) are compressed by determining an approximate or exact region in each image corresponding to air (e.g., based on HU value, based on location, based on volume, etc.) and setting the air region (e.g., voxels corresponding to the air region, pixels corresponding to the air region, etc.) to have a fixed value. Additionally or alternatively, any non-critical region (e.g., bone, unaffected region, etc.) or other region can be altered (e.g., set to a fixed value, removed, etc.) during the compression. In a specific example, for instance, a set of voxels corresponding to air are set to all have a common fixed value (e.g., an upper limit value, a lower limit value, a value between 0 and 1, a predetermined value, etc.).

In some variations, S240 includes identifying an optimal visualization to be transmitted (e.g., from a remote computing system) and received (e.g., at a user device), which functions to prepare an optimal output for a $2^{nd}$ point of care (e.g., specialist), reduce the time required to review the data packet, bring attention to the most relevant image data, or to effect any other suitable outcome.

In some variations, this is involves a reverse registration process. In a specific example, for instance, this is done through maximum intensity projection (MIP), where an optimal range of instances is determined based on which images contain the largest percentage of the segmented anatomical region of interest in a MIP image.

Additionally or alternatively, S240 can include removing and/or altering (e.g., encrypting) metadata or any unnecessary, private, confidential, or sensitive information from the data packet. In some variations, patient information (e.g., patient-identifiable information) is removed from the data packet in order to comply with regulatory guidelines. In other variations, all metadata are extracted and removed from the data packet.

In some variations, S240 includes storing a dataset (e.g., at a remote server, at a local server, at a PACS server, etc.). In one example, metadata are extracted from the image data and stored separately from image data in a relational database. In another example, any or all of the data packet are stored (e.g., temporarily, permanently, etc.) to be used in one or more future analytics processes, which can function to improve the method, better match patients with suitable treatment options, or for any other suitable purpose.

In some variations, S240 includes applying a low bandwidth implementation process, which can function to reduce the time until a specialist receives a first piece of data or data packet (e.g., an incomplete series, incomplete study, single instance, single image, optimal image, image showing occlusion, etc.), reduce the processing required to inform a specialist of a potential patient condition, reduce the amount of data required to be reviewed by a specialist, reduce the amount of data being transmitted from a remote computing system to a mobile device, or perform any other suitable function. The low bandwidth implementation process can include any or all of: organizing (e.g., chunking) data (e.g., chunking a series of images based on anatomical region), reordering data (e.g., reordering slices in a CT series), transmitting a portion (e.g., single image, single slice, etc.) of a data packet (e.g., series, study, set of images, etc.) to a device (e.g., user device, mobile device, healthcare facility workstation, computer, etc.), sending the rest of the data packet (e.g., only in response to a request, after a predetermined time has passed, once the data packet has been fully processed, etc.), or any other process. In a specific example, for instance, the image data (e.g., slices) received at a remote computing system from a scanner are chunked, reordered, and a single slice is sent to the device associated with a specialist first (e.g., prior to sending a remaining set of slices).

Additionally or alternatively, S240 can include any other suitable steps performed in any suitable order.

The method can additionally or alternatively include any other suitable sub-steps for preparing the data packet.

4.7 Method—Transmitting Information to a Device Associated with the $2^{nd}$ Point of Care S250

Figure 6:
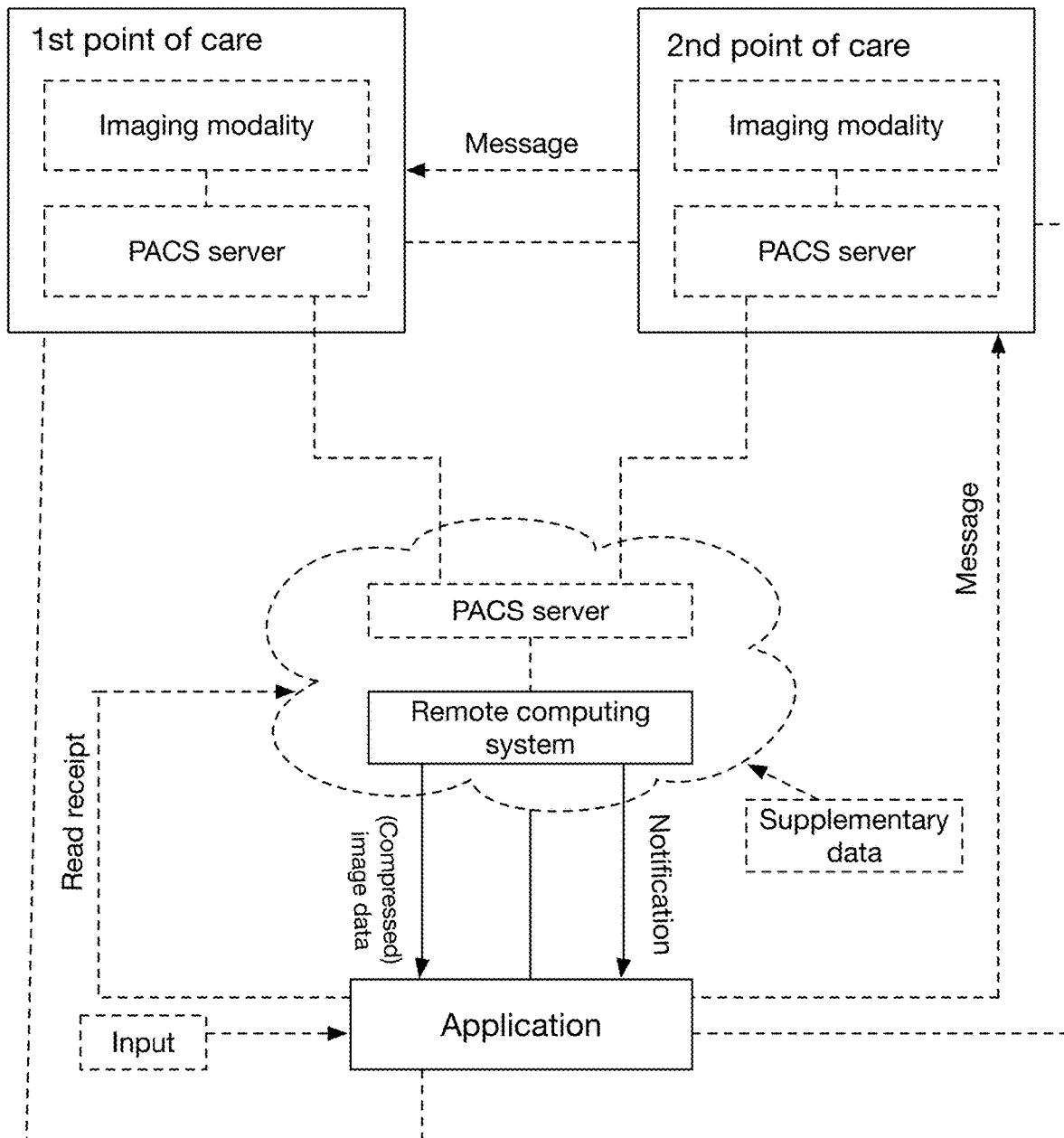
FIG. 6 depicts a variation of a method for computer-aided triage.

Transmitting information to a device associated with the $2^{nd}$ point of care (e.g., specialist, contact, etc.) S250 (e.g., as shown in FIG. 6) functions to initiate a pull from a $1^{st}$ point of care to a $2^{nd}$ point of care, which can decrease time to care, improve quality of care (e.g., better match between patient condition and specialist), or have any other suitable outcome. Preferably, the $2^{nd}$ point of care is a hub facility (e.g., specialist facility, interventional center, comprehensive stroke center, etc.). In some variations, the $1^{st}$ point of care (e.g., healthcare facility at which patient initially presents) also functions as the $2^{nd}$ point of care, such as when a suitable specialist is associated with the $1^{st}$ point of care, the $1^{st}$ point of care is a hub (e.g., specialist facility, interventional center, comprehensive stroke center, etc.), it is not advised to transfer the patient (e.g., condition has high severity), or for any other reason.

S250 is preferably performed after (e.g., in response to) a $2^{nd}$ point of care is determined, but can additionally or alternatively be performed after a data packet (e.g., compressed data packet, encrypted data packet, etc.) has been determined, multiple times throughout the method (e.g., to multiple recipients, with multiple data packets, with updated information, after a predetermined amount of time has passed since a notification has been sent to a first choice specialist, etc.), or at any other time during the method 200.

The device is preferably a user device, further preferably a mobile device. Examples of the user device include a tablet, smartphone, mobile phone, laptop, watch, wearable device (e.g., glasses), or any other suitable user device. The user device can include power storage (e.g., a battery), processing systems (e.g., CPU, GPU, memory, etc.), user outputs (e.g., display, speaker, vibration mechanism, etc.), user inputs (e.g., a keyboard, touchscreen, microphone, etc.), a location system (e.g., a GPS system), sensors (e.g., optical sensors, such as light sensors and cameras, orientation sensors, such as accelerometers, gyroscopes, and altimeters, audio sensors, such as microphones, etc.), data communication system (e.g., a WiFi module, BLE, cellular module, etc.), or any other suitable component.

The device is preferably associated (e.g., owned by, belonging to, accessible by, etc.) a specialist or other individual associated with the $2^{nd}$ point of care, but can additionally or alternatively be associated with an individual or computing system at the $1^{st}$ point of care, the patient, or any other suitable individual or system.

In one variation, the device is a personal mobile phone of a specialist. In another variation, the device is a workstation at a healthcare facility (e.g., first point of care, second point of care, etc.).

The information preferably includes a data packet, further preferably the data packet prepared in S240. Additionally or alternatively, the information can include a subset of a data packet, the original data packet, any other image data set, or any other suitable data. The information further preferably includes a notification, wherein the notification prompts the individual to review the data packet at the device (e.g., a message reciting "urgent: please review!"). Additionally or alternatively, the notification can prompt the individual to review data (e.g., original data packet, uncompressed images, etc.) at a separate device, such as a workstation in a healthcare facility, a PACS server, or any other location. Further additionally or alternatively, the notification can include any suitable information, such as, but not limited to: instructions (e.g., for treating patient, directions for reaching a healthcare facility), contact information (e.g., for emergency physician at first point of care, administrative assistant, etc.), patient information (e.g., patient history), or any other suitable information.

The notification preferably includes an SMS text message but can additionally or alternatively include an email message, audio message (e.g., recording sent to mobile phone), push notification, phone call, or any other suitable notification.

The information is preferably sent to the device through a client application executing on the user device but can additionally or alternatively be sent through a messaging platform, web browser, or other platform.

In some variations, a notification is sent which prompts the individual to provide an input, wherein the input can indicate that the individual will view, has viewed, or is in the process of viewing the information (e.g., image data), sees the presence of a condition (e.g., true positive, serious condition, time-sensitive condition, etc.), does not see the presence of a condition (e.g., false positive, serious condition, time-sensitive condition, etc.), has accepted treatment of the patient (e.g., swipes right, swipes up, clicks a check mark, etc.), has denied treatment of the patient (e.g., swipes left, swipes down, clicks an 'x', etc.), wants to communicate with another individual (e.g., healthcare worker at $1^{st}$ point of care), such as through a messaging platform (e.g., native to the device, enabled by the client application, etc.), or any other input. In some variations, one or more additional notifications are provided to the individual (e.g., based on the contents of the input), which can be determined by a lookup table, operator, individual, decision engine, or other tool. In one example, for instance, if the individual indicates that the condition is a true positive, information related to the transfer of the patient (e.g., estimated time of arrival, directions to the location of the patient, etc.) can be provided (e.g., in a transfer request, wherein patient transfer to a specified location, such as the $2^{nd}$ point of care, can be initiated upon transfer request receipt). In some variants, the data (e.g., images) are displayed on the user device (e.g., mobile device, workstation) in response to user interaction with the notification (e.g., in response to input receipt). However, the input can trigger any suitable action or be otherwise used.

Additionally or alternatively, an input can automatically be received from the client application, such as a read receipt when the individual has opened the data packet, viewed the notification, or interacted with the client application in any other suitable way. In one example, if a read receipt is not received (e.g., at the remote computing system) from the device within a predetermined amount of time (e.g., 10 seconds), a second notification and/or data packet (e.g., compressed set of images) are sent to a second individual (e.g., second choice specialist based on a lookup table).

In some variations, various outputs can be sent from the client application (e.g., at the user device) to one or more recipients (e.g., to a second user device, client application on a work station, on a computing system, etc.), such as recipients associated with a first point of care (e.g., radiologists, emergency physicians, etc.). The outputs can be determined based on the inputs received at the client application associated with the individual (e.g., acceptance of case, verification of true positive, etc.), based on a lookup table, or otherwise determined. The outputs preferably do not alter the standard radiology workflow (e.g., are not shared with radiologists; radiologists are not notified), which functions to ensure that the method 200 is a true parallel process, and that the standard radiology workflow results in an independent assessment of the patient, but can additionally or alternatively cut short a workflow, bring a specialist in on the patient case earlier than normal, or affect any other process in a healthcare facility.

4.8 Method—Aggregating Data S260

The method 200 can optionally include any number of sub-steps involving the aggregation of data involved in and/or generated during the method 200, which can function to improve future iterations of the method 200 (e.g., better match patients with a specialist, decrease time to treat a patient, increase sensitivity, increase specificity, etc.). The aggregated data is preferably used in one or more analytics steps (e.g., to refine a treatment option, make a recommendation for a drug or procedure, etc.), but can additionally or alternatively be used for any other suitable purpose.

In some variations, for instance the outcomes of the patients examined during the method 200 are recorded and correlated with their corresponding data packets, which can be used to assess the success of the particular treatment options chosen and better inform treatment options in future cases.

4.9 Method—Variations

In one variation, the method functions to augment a standard radiology workflow operating in parallel with the method, which can include any or all of: at a remote computing system (e.g., remote from the first point of care), receiving a set of images (e.g., of a brain of the patient), wherein the set of images is concurrently sent to the standard radiology workflow operating in parallel with the method and automatically detecting a condition (e.g., potential large vessel occlusion) from the set of images. Upon condition detection, the method can include any or all of, automatically: determining a second specialist from the standard radiology workflow, wherein the specialist is associated with a second point of care; notifying the second specialist on a mobile device associated with the second specialist before the radiologist notifies the first specialist; and displaying a compressed version of the set of images on the mobile device.

In a specific example, the method includes, at a remote computing system, receiving a set of Digital Imaging and Communications in Medicine (DICOM) brain images associated with the patient, wherein the set of DICOM brain images is concurrently sent to a standard radiology workflow operating in parallel with the method. In the standard radiology workflow, the radiologist analyzes the set of DICOM brain images and notifies a specialist based on a visual assessment of the set of DICOM brain images at the workstation, wherein the standard radiology workflow takes a first amount of time. The method can then include detecting a potential cerebral artery occlusion from the set of DICOM brain images, which includes any or all of: identifying a large vessel region from the set of DICOM brain images; extracting a centerline from the large vessel region; determining a centerline length of the large vessel region based on the centerline; comparing the centerline length with a predetermined threshold; and detecting the potential cerebral artery occlusion when the centerline length is less than the predetermined threshold. Upon potential cerebral artery occlusion detection, the method can include, automatically: determining the specialist from the standard radiology workflow, wherein the specialist is associated with a second point of care; notifying the specialist on a mobile device associated with the specialist, wherein the specialist is notified in a second amount of time shorter than the first amount of time, wherein the radiologist is not automatically notified upon potential cerebral artery occlusion detection; displaying a compressed version of the set of DICOM brain images on the mobile device; and displaying a high-resolution version of the set of DICOM brain images on a workstation associated with the specialist. Additionally or alternatively, the method can include any other suitable process.

In another variation, the method functions to determine a specialist (e.g., independently of the performance of a radiology workflow, in parallel with a radiologist workflow, bypassing a radiologist workflow, etc.), where the method includes: receiving a data packet comprising a set of images (e.g., CT images of a brain of the patient) sampled at the first point of care, where the data packet is concurrently sent to the standard radiology workflow; determining an anatomical feature (e.g., large vessel region) from the set of images; extracting a feature (e.g., large vessel centerline) from the region; determining a parameter (e.g., calculating a centerline length) of the feature; and comparing the parameter (e.g., centerline length) with a predetermined threshold. In one example, the method can then include detecting a large vessel occlusion when the centerline length is less than the predetermined threshold. In response to the detection of a condition (e.g., large vessel occlusion detection), the method can include any or all of: presenting a notification on a mobile device associated with a specialist from the standard radiology workflow, the specialist associated with a second point of care, displaying a compressed version of the set of images on the mobile device in response to interaction with the notification, or any other suitable process.

In a specific example, the method includes: receiving, at a remote computing system, a data packet from the first point of care, the data packet including a set of computed tomography (CT) images and a set of metadata associated with the set of CT images; processing the data packet at the remote computing system, which can include any or all of: organizing the set of CT images into a series based on the metadata, identifying soft matter voxels from the series based on a soft matter mask, the soft matter mask including a predetermined Hounsfield Unit (HU) threshold, registering the soft matter voxels to a set of reference CT images, thereby determining a registered set of voxels, segmenting (e.g., with a feed-forward deep convolutional network) a large vessel region in the registered set of voxels, extracting a centerline of the segmented large vessel region, and determining a length of the segmented large vessel region based on the centerline. With the centerline length, the method can then include: comparing the centerline length with a predetermined threshold, wherein the predetermined threshold is greater than a corresponding anatomical length. When the centerline length is less than the predetermined threshold, a specialist can be determined based on a lookup table. Then, a notification and a second data packet comprising a set of compressed images can be transmitted to a user device associated with the specialist.

Figure 7:
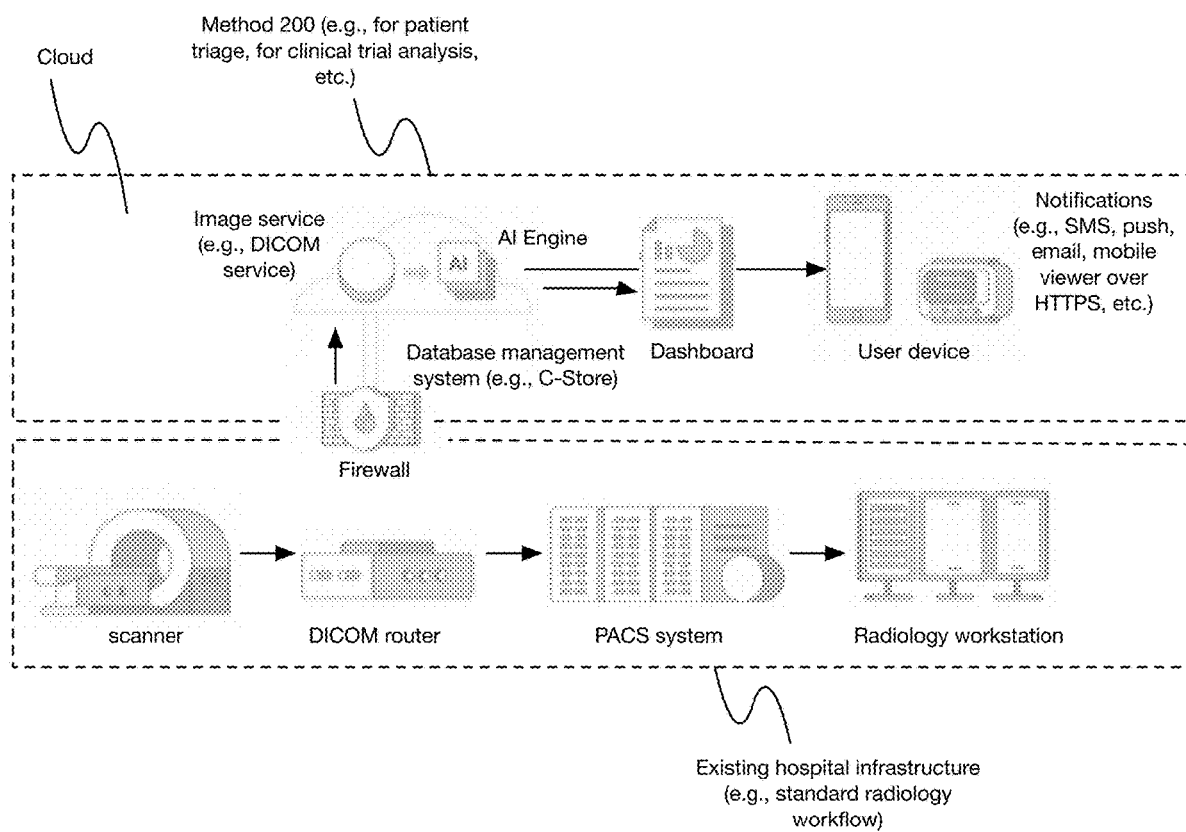
FIG. 7 depicts a variation of a method for computer-aided triage for clinical trial recommendation and/or for treatment.
Figure 8:
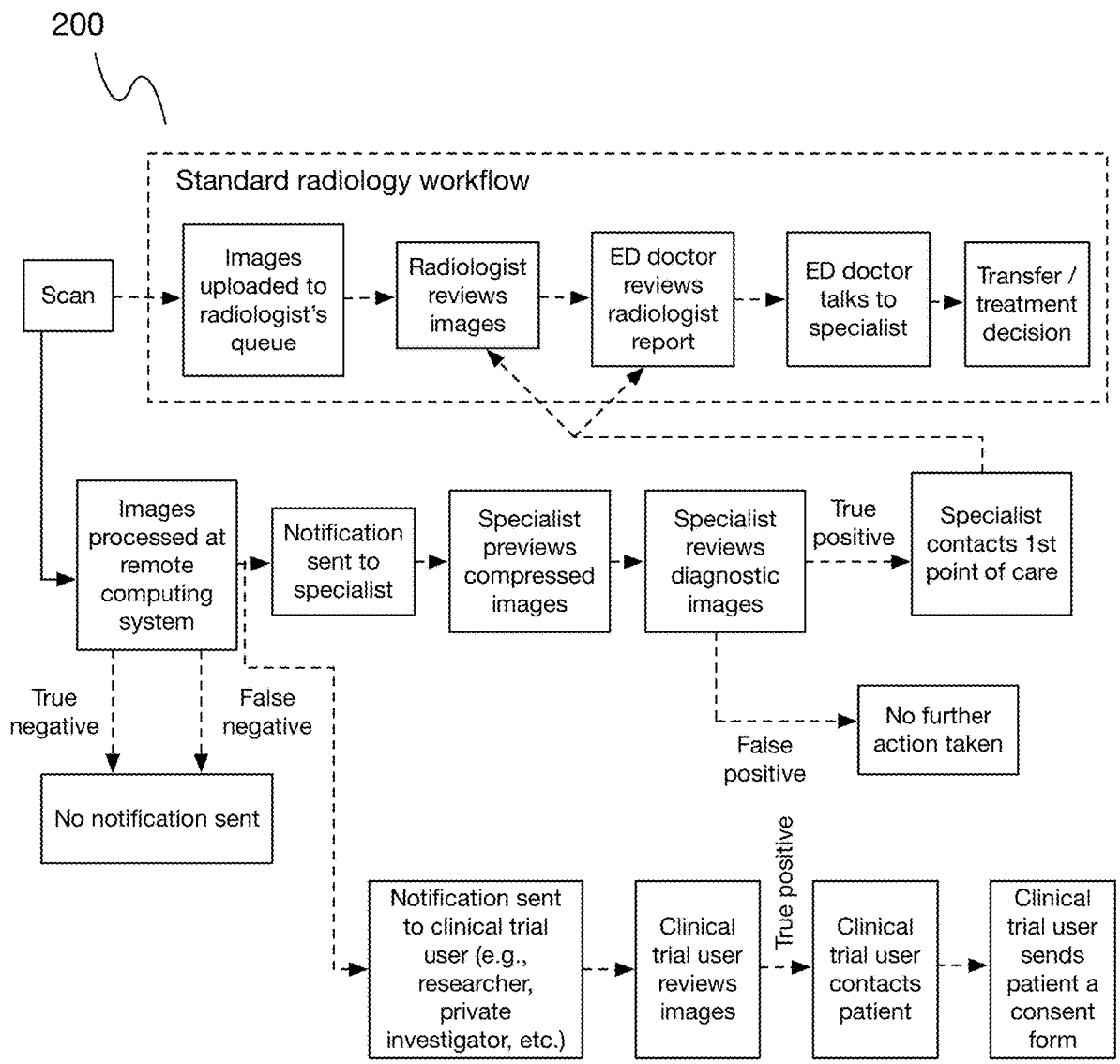
FIG. 8 depicts a variation of a method for computer-aided triage for clinical trial recommendation and/or for treatment.
Figure 9:
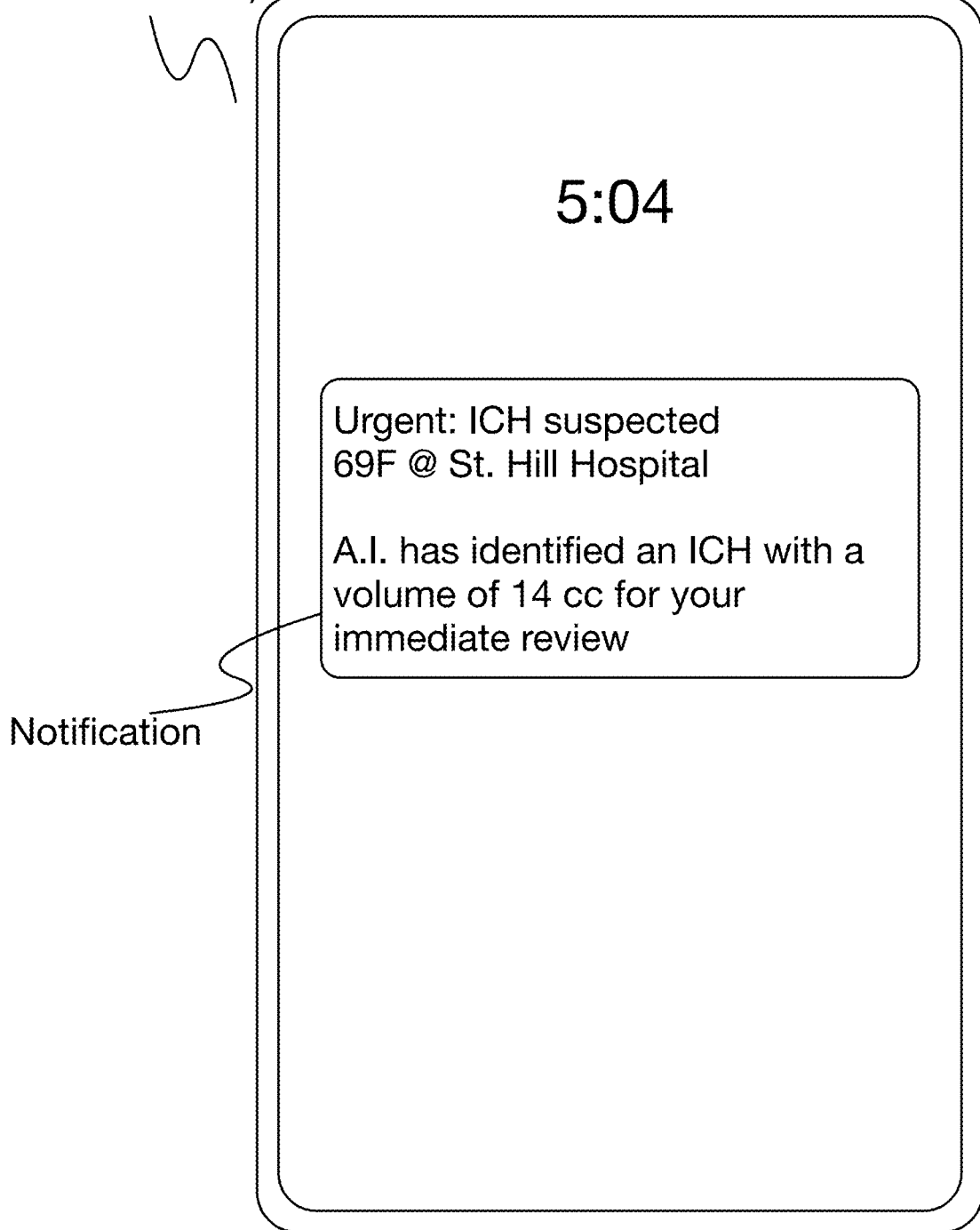
FIG. 9 depicts a variation of an application on a user device (e.g., a user device of a research coordinator of a clinical trial).

In yet another variation (e.g., as shown in FIG. 8, as performed in accordance with the system shown in FIG. 7, etc.), additional or alternative to those described above, the method functions to evaluate if a patient presenting with a potential pathology (e.g., stroke, ICH, LVO, etc.) qualifies for a clinical trial and if so, to alert (e.g., automatically, in a time period shorter than a determination made by a radiologist in a standard radiology workflow, etc.) a research coordinator associated with the clinical trial, wherein the method includes: receiving a data packet comprising a set of images (e.g., CT images of a brain of the patient) sampled at the first point of care, where the data packet is concurrently sent to the standard radiology workflow; determining an anatomical feature (e.g., large vessel region) from the set of images; determining a parameter (e.g., calculating a volume, calculating a centerline length, etc.) of the feature; comparing the parameter (e.g., centerline length) with set of clinical trial criteria (e.g., inclusion criteria, exclusion criteria, etc.); and in an event that the parameter satisfies the clinical trial criteria (e.g., according to a set of thresholds), presenting a notification on a mobile device associated with the research coordinator (e.g., as shown in FIG. 9). If the research coordinator decides to include the patient in the clinical trial (e.g., based on the notification, based on a set of compressed images sent to a user device of the research coordinator, based on a calculated parameter, etc.), the research coordinator can optionally transmit a consent form to the patient (e.g., to a user device of the patient, to a workstation associated with the $1^{st}$ point of care, to a workstation associated with the $2^{nd}$ point of care, etc.) and/or to a healthcare worker (e.g., to a user device of the healthcare worker, to a workstation of the healthcare worker, etc.), such as a surgeon, associated with the patient (e.g., via a client application executing on a user device of the research coordinator, from a remote computing system, etc.). Additionally or alternatively, the research coordinator can communicate (e.g., via a HIPAA-compliant messaging platform established through the client application, through a text messaging application, etc.) with a physician associated with the patient, and/or otherwise review and communicate information.

Additionally or alternatively, the method can include any other steps performed in any suitable order.

Although omitted for conciseness, the preferred embodiments include every combination and permutation of the various system components and the various method processes, wherein the method processes can be performed in any suitable order, sequentially or concurrently.

As a person skilled in the art will recognize from the previous detailed description and from the figures and claims, modifications and changes can be made to the preferred embodiments of the invention without departing from the scope of this invention defined in the following claims.

We claim:

1. A method for computer-aided triage, the method comprising, during triage of a patient:
   receiving, at a computing system associated with a first point of care, a set of images associated with the patient and taken at the first point of care;
   at the computing system, automatically detecting a potential pathology from the set of images based on an automated processing of the set of images;
   upon detecting the potential pathology from the set of images, automatically:
      determining, at the computing system, a clinical trial associated with the potential pathology;
      selecting, at the computing system, a research coordinator from a set of multiple research coordinators based on the clinical trial;
      notifying the research coordinator on a first mobile device associated with the research coordinator;
      displaying a compressed version of the set of DICOM images on the first mobile device;
      receiving an input from the research coordinator at the first mobile device; and
      establishing a communication between the research coordinator and a specialist via a first client application executing on the first mobile device and a second client application executing on a second mobile device of the specialist.

2. The method of claim 1, further comprising:
   determining, at the computing system, the specialist:
   notifying the specialist at the first mobile device; and
   displaying the compressed version of the set of images on the first mobile device.

3. The method of claim 2, wherein the specialist is associated with a second point of care.

4. The method of claim 3, wherein the first input initiates a transfer request of the patient from the first point of care to the second point of care upon transfer request receipt.

5. The method of claim 4, wherein the communication comprises a notification to the first client application, wherein the notification comprises information associated with the transfer.

6. The method of claim 5, wherein the information associated with the transfer comprises an estimated time of arrival of the patient at the second point of care.

7. The method of claim 1, wherein the input comprises a trigger, wherein the trigger initiates a consent form to be transmitted to the patient.

8. The method of claim 1, wherein the computing system is a remote computing system remote from the first point of care.

9. A method for computer-aided triage, the method comprising, during triage of a patient:
   receiving, at a computing system associated with a first point of care, a set of images associated with the patient and taken at the point of care;
   detecting a potential pathology from the set of images;
   upon detecting the potential pathology from the set of images, automatically:
      determining, at the computing system, a clinical trial associated with the potential pathology;
      determining, at the computing system, a research coordinator associated with the clinical trial;
      notifying the research coordinator on a first mobile device associated with the research coordinator;
   receiving an input from the research coordinator at the computing system, wherein the input comprises an acceptance of enrolling the patient in the clinical trial; and
   in response to receiving the acceptance, establishing a communication between a specialist and the research coordinator, wherein establishing the communication comprises enabling messaging between the specialist and the research coordinator via a first client application executing on the first mobile device and a second client application executing on a second mobile device associated with the specialist.

10. The method of claim 9, further comprising establishing communication between the first research coordinator and a second research coordinator.

11. The method of claim 9, further comprising displaying a second set of images on the first mobile device, wherein the second set of images is a compressed version of the first set of images.

12. The method of claim 9, further comprising displaying a second set of images on the first mobile device, wherein the second set of images is an annotated version of the first set of images.

13. The method of claim 9, wherein the input comprises a trigger, wherein the trigger initiates a consent form associated with the clinical trial to be transmitted to the patient.

14. The method of claim 13, wherein the input is received from the research coordinator at the first client application.

15. The method of claim 9, further comprising calculating, at the computing system, a value of a parameter associated with the potential pathology and comparing the value with a set of predetermined criteria.

16. The method of claim 15, wherein the potential pathology comprises an intracerebral hemorrhage, and wherein the parameter comprises a volume.

17. The method of claim 9, further comprising, upon detecting the potential pathology from the set of images, automatically:
   determining, at the remote computing system, a specialist associated with a second point of care; and
   notifying the specialist at a mobile device associated with the specialist, wherein the specialist is notified in a second amount of time shorter than the first amount of time.

18. The method of claim 9, further comprising receiving an input from the specialist, wherein the input initiates a transfer request.

19. The method of claim 9, wherein detecting the potential pathology comprises, at the computing system, automatically detecting the potential pathology from the set of images based on an automated processing of the set of images.

20. The method of claim 7, further comprising:
   receiving a signed version of the consent form; and
   in response to receiving the signed version of the consent form, enabling access to additional patient information at the first mobile device.

* * * * *